United States Patent [19]

Tisdale et al.

[11] Patent Number: 5,420,115

[45] Date of Patent: May 30, 1995

[54] METHOD FOR THE TREATMENT OF PROTOZA INFECTIONS WITH $2^1$-DEOXY-$2^1$-FLUOROPURINE NUCLEOSIDES

[75] Inventors: Sylvia M. Tisdale, Beckenham, England; Joel Van Tuttle, Durham, N.C.; Martin J. Slater, Beckenham, England; Susan M. Daluge, Chapel Hill, N.C.; Wayne H. Miller, Apex, N.C.; Thomas A. Krenitsky; George W. Koszalka, both of Chapel Hill, N.C.

[73] Assignee: Burroughs Wellcome Co., N.C.

[21] Appl. No.: 940,304

[22] Filed: Sep. 2, 1992

Related U.S. Application Data

[63] Continuation of Ser. No. 580,105, Sep. 10, 1990, abandoned.

[51] Int. Cl.$^6$ .................. A61K 31/70; C07H 19/173
[52] U.S. Cl. ........................ 514/46; 514/45; 536/27.61; 536/27.81
[58] Field of Search ...................... 514/45–46; 536/27.61–27.81

[56] References Cited

U.S. PATENT DOCUMENTS

| | | | |
|---|---|---|---|
| 4,145,531 | 3/1979 | Eckstein et al. | 536/27.11 |
| 5,126,506 | 6/1992 | Sterzycki et al. | 536/27.81 |

FOREIGN PATENT DOCUMENTS

| | | |
|---|---|---|
| 219829 | 10/1985 | European Pat. Off. . |
| 0219829 | 4/1987 | European Pat. Off. . |
| 285432 | 3/1988 | European Pat. Off. . |
| 0287313 | 10/1988 | European Pat. Off. . |
| WO89/08658 | 9/1989 | WIPO . |

OTHER PUBLICATIONS

Uesugi, Seiichi, et al.; Synthesis and Characterization of Dinucleoside Monophosphates Containing 2'-Halo-2'-Deoxyadenosines; pp. 851–859; 1981; Nippon Kagau Kaishi, Japan.

Ikehara, Morio, Heterocycles, vol. 21, No. 1, 1984, pp. 75–90.

Cheng et al., Biopolymers, vol. 22, 1983, pp. 1427–1444.

Ikehara et al. Chem. Pharm. Bull. 29, (9), 1881, pp. 2408–2412.

Uesugi et al. Biopolymers, vol. 22, 1983, pp. 1189–1202.

Chem. Pharm. Bull. 29, (11), 1981, pp. 3281–3285.

John A. Montgomery, et al.; vol. 80; pp. 404–408; Jan. 20, 1958 Synthesis of potential anticancer agents. XI. $N^{2,6}$-Alkyl Derivatives of 2,6-Diaminopurine$^2$; Contribution from the Kettering-Meyer Laboratory, $^1$Souther Research Institute.

Michael Bessodes, et al.; Crown ether catalyzed 0-alkylation of carbohydrates and nucleosides; pp. 560–564; Jul. 1988; Institut de Recherches Scientificques sur le Cancer, BP8, F-94802 Villejuif, France.

*Primary Examiner*—Douglas W. Robinson
*Assistant Examiner*—Gary L. Kunz
*Attorney, Agent, or Firm*—Donald Brown; Hanna H. Green

[57] ABSTRACT

A method for treating two specific protozoal infections, *Trichomonas vaginalis* and *Giardia lamblia*, comprising the administration to a mammal in need thereof one of the following purine nucleosides:

2,6-diamino-9-(2-deoxy-2-fluoro-$\beta$-D-ribofuranosyl)-9H-purine 2-amino-9-(2-deoxy-2-fluoro-$\beta$-D-ribofuranosyl)-9H-purine 2-amino-9-(2-deoxy-2-fluoro-$\beta$-D-ribofuranosyl)-6-methoxy-9H-purine.

6 Claims, No Drawings

METHOD FOR THE TREATMENT OF PROTOZA INFECTIONS WITH 2¹-DEOXY-2¹-FLUOROPURINE NUCLEOSIDES

This is a continuation of application Ser. No. 07/580,105, filed on Sep. 10, 1990, now abandoned.

The present invention relates to chemical compounds having anti-infectious activity, to methods for their preparation, to compositions containing them and their use particularly in the treatment of parasitic and viral diseases. More particularly the invention relates to 2'-deoxy-2'-fluoro-ribonucleosides and derivatives thereof.

In the field of antiviral chemotherapy, few drugs exist which effectively combat the virus per se, owing to the difficulty of attacking the virus while leaving uninfected host cells unimpaired. It has recently been established that certain stages in the virus life-cycle, which vary from species to species, are specified by the virus itself. However, owing to great similarity between viral and host functions, effective treatments have proved very difficult to identify.

One group of viral pathogens which have afflicted man since ancient times and have been responsible for the deaths of many millions of people through the centuries are the influenza viruses. These viruses, particularly influenza A and B, remain one of the major causative agents of acute respiratory illness in the world to day.

Influenza viruses are members of the family of negative strand viruses Orthomyxoviridae. Another negative strand virus having important health implications is respiratory syncytial virus (RSV), which is a *pneumovirus*, a genus of the family Paramyxoviridae. RSV is a major cause of lower respiratory tract illness during infancy and childhood.

Fluorinated nucleosides have been previously proposed for the treatment of viral and parasitic diseases. For example, EP-A-O 287 313 discloses 2',3'-dideoxynucleosides, substituted with fluorine in the 2'position for use in the treatment of human immunodeficiency virus. EP-A-O 219 829 discloses 2'-deoxy-2'-fluoro-β-D-arabino-furanosyl nucleosides for use as antiparasitic agents, especially against leishmaniasis. Processes for the preparation of certain 2'-fluoro-2'-deoxy-ribonucleosides have been described by Uesugi et al., (Nucleosides and Nucleotides 2, 373-, 1983) and Ikehara et al., (Chem. Pharm. Bull. 29, 1034-, 1981).

We have now found that compounds of the formula (I) and their pharmaceutically acceptable salts are anti-infective agents, particularly against viruses. For example, the compounds of formula (I) are active against influenza virus, particularly influenza A and B and RSV infections, and certain protozoa, for example, *Trichomonas vaginalis* and *Giardia lamblia*. In formula (I):

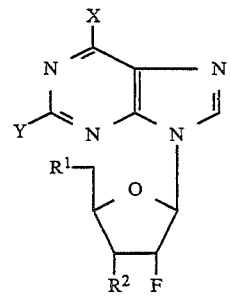

Y is either H or $NH_2$;

X is a group $-NR^3R^4$ in which $R^3$ and $R^4$ may be the same or different and each represent hydrogen, $C_{1-6}$ alkyl, $C_{2-6}$ alkenyl, $C_{3-7}$ cycloalkyl, each group optionally being substituted by one or more halogen, or X is a group $Z-R^5$ in which Z is oxygen or sulphur and $R^5$ has the same definition as $R^3$, or X is halogen or hydrogen; and $R^1$ and $R^2$, which may be the same or different, each represent:
  a hydroxy group;
  a group $-OCOR^6H$ where $R^6$ is a divalent group which is straight or branched $C_{1-6}$ alkylene, $C_{2-6}$ alkenylene or $C_{3-7}$ cycloalkylene, each being optionally substituted by one or more hydroxy groups;
  a group $-OCO_2R^7H$ where $R^7$ is a covalent bond or is as defined for $R^6$;
  a group $-OCOR^6-COOR^8$ where $R^6$ is as defined above and $R^8$ is selected from hydrogen, straight or branched chain $C_{1-6}$ alkyl or $C_{1-6}$ alkenyl each being optionally substituted by one or more hydroxy groups;
  a group $-OCOR^7-Z-Ar$ where $R^7$ is as defined above, Z is either a covalent bond or oxygen and Ar is an aromatic ring, for example, a monocyclic aryl (e.g. phenyl) or a heteroaryl (e.g. pyridine), unsubstituted or substituted by one or more halogen, $C_{1-6}$ alkyl or $C_{1-6}$ alkoxy;
  a group $-OR^6H$ where $R^6$ is as defined above;
  a group $-OR^6-Z-Ar$ where $R^6$, Z and Ar are as defined above;
  a group $-OCOCHR^9NR^{10}R^{11}$ where $R^{10}$ and $R^{11}$ are as defined for $R^8$, and $R^9$ is
  hydrogen,
    straight or branched chain $C_{1-4}$ alkyl optionally substituted by one or more hydroxy, mercapto, $C_{1-3}$ alkoxy or $C_{1-3}$ alkylthio groups,
    a group-$R^{12}$—A where $R^{12}$ is a $C_{1-4}$ alkylene group optionally substituted by one or more hydroxy groups and A is a group $-COOH$, $-CONH_2$, $-NH_2$ or $-NH-C(NH)NH_2$ or A is a 4- to 11-membered aromatic or non-aromatic cyclic or heterocyclic ring system containing 3 to 10 carbon atoms and 0,1,2 or 3 ring nitrogen atoms, the ring carbon atoms and/or nitrogen atoms being optionally substituted by one or more hydroxy groups;
  a group $-OCO-R^{13}$ where $R^{13}$ is a 4- to 7-membered heterocyclic ring containing 3 to 6 carbon atoms and 0, 1 or 2 nitrogen atoms, the ring carbon atoms and/or nitrogen atoms being optionally substituted by one or more hydroxy groups; or
  a mono-, di- or tri-phosphate ester group.

The present invention further includes compounds of formula (I) and their salts for use in medical therapy.

Preferred ester groups of the formula —O-COCHR$^9$NR$^{10}$R$^{11}$ and —OCO—R$^{13}$ are esters of naturally occurring α-amino acids included by the above definition. Especially preferred ester groups of the formula —OCOCHR$^9$NR$^{10}$R$^{11}$ are those wherein R$^9$ is C$_{1-4}$ alkyl group and R$^{10}$ and R$^{11}$ are both hydrogen, for example, valine or alanine.

It will be appreciated that the compounds of Formula (I) may exist in various tautomeric forms, and that when X is a group —OH, it may also represent an oxo group. Compounds of formula (I) and their salts may also exist in α or β anomeric forms. The present invention therefore includes within its scope each of the individual α and β anomers of the compounds of formula (I) and mixtures thereof.

The compounds of formula (I) and their pharmaceutically acceptable salts will be hereinafter referred to as the compounds according to the invention. The term "active ingredient" as used hereafter, unless the context requires otherwise, refers to a compound according to the invention.

The activity of the active ingredients against influenza A and B has not previously been known and the present invention also provides pharmaceutical formulations comprising a compound of formula (I) or a pharmaceutically acceptable salt thereof, especially useful for inhibiting the growth of influenza A or B in mammals and man. We therefore provide solid formulations comprising active ingredient and a solid carrier, or an inhalable formulation comprising active ingredient and inhalable fluid carrier.

The present invention further includes:
a) a method for the treatment or prophylaxis of a viral infection particularly influenza virus or RSV infection or a protozoal infection, for example, *Trichomonas vaginalis* or *Giardia lamblia*, in a host, for example a mammal including man, and mice which comprises treating said mammal with an effective non-toxic amount of a compound according to the invention.
b) use of a compound according to the invention in the manufacture of a medicament for the treatment or prophylaxis of an infection including a viral infection particularly influenza virus or RSV infection or a protozoal infection, for example, *Trichomas vaginalis* or *Giardia lamblia*.

Certain of the formula (I) compounds and their salts are new compounds and such new compounds and salts are a further aspect of the present invention. The new compounds are those, as defined above for formula (I) except for those in which R$^1$ and R$^2$ are each hydroxy or R$^1$ is a mono-, di- or tri-phosphate 5'-ester and R$^2$ is hydroxy or R$^1$ is hydroxy and R$^2$ is a mono-, di- or tri-phosphate 3'-ester and either (a) X is OH and Y is NH$_2$ or H or (b) X is NH$_2$ and Y is H.

Preferred compounds according to the invention include those wherein R$^1$ and R$^2$ are either both OH or R$^1$ is a monophosphate and R$^2$ is OH, Y is H or NH$_2$ and X is a group —NR$^3$R$^4$ in which R$^3$ and R$^4$, which may be the same or different, represent H, C$_{1-6}$ alkyl, or X is a group Z—R$^5$ in which Z is O or S and R$^5$ is C$_{1-6}$ alkyl, or X is a halogen or hydrogen.

Particularly preferred compounds of formula (I) include those in which R$^1$ and R$^2$ are both OH, Y is NH$_2$ and X is H, OH, NH$_2$ or Z—R$^5$ where Z is O and R$^5$ is C$_{1-6}$ alkyl.

Examples of especially preferred compounds of formula (I) are:
(1) 2,6-Diamino-9-(2-deoxy-2-fluoro-β-D-ribofuranosyl)-9H-purine.
(2) 2-Amino-9-(2-deoxy-2-fluoro-β-D-ribofuranosyl)-9H-purine.
(3) 9-(2-deoxy-2-fluoro-β-D-ribofuranosyl)guanine.
(4) 2-Amino-9-(2-deoxy-2-fluoro-β-D-ribofuranosyl)-6-methoxy-9H-purine.

The present invention further includes a process for the preparation of the novel compounds of the formula (I) and pharmaceutically acceptable salts thereof which comprises either:
(A) reacting a purine base of formula PuH wherein Pu represents the purine residue:

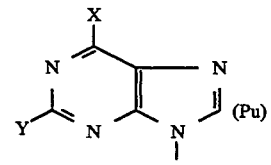

(wherein X and Y are as described above), or a salt thereof, with a compound of formula (II)

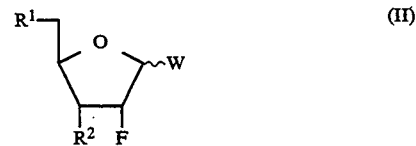

wherein R$^1$ and R$^2$ are as hereinbefore defined, and W is either a phosphate ester or salt thereof or a purine or pyrimidine moiety (other than Pu) to form a compound of formula (I);

(B) reacting a compound of formula (III)

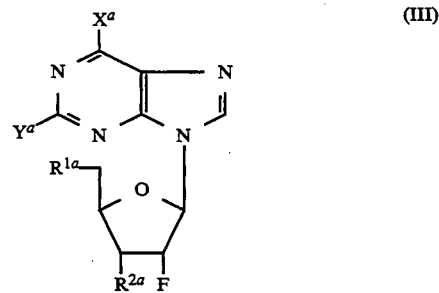

(wherein X$^a$, Y$^a$, R$^{1a}$ and R$^{2a}$ respectively represent the groups X, Y, R$^1$ and R$^2$ as defined above or a precursor, e.g. protected, form of such a group providing at least one of X, Y, R$^1$ and R$^2$ represents a precursor form) with an agent serving to convert the said precursor form of the group(s) to the desired group(s);

(i) reacting a compound of formula (I) wherein at least one of R$^1$ and R$^2$ is a hydroxy group with an appropriate agent serving to convert the said hydroxy group to an alternative group represented by R$^{1a}$ and R$^{2a}$.

(ii) reacting a compound of formula (I) wherein R$^1$ and/or R$^2$ are not hydroxy with an agent serving to convert the said $R^1$ and/or $R^2$ group to a hydroxy group.

Process (A), which is particularly suitable for the preparation of compounds of formula (I) wherein $R^1$ and $R^2$ are both hydroxy and Y is H or $NH_2$, may be effected enzymatically by reacting the purine base of formula Pu wherein X and Y are as hereinbefore defined, or a salt thereof, with a compound of formula (II)

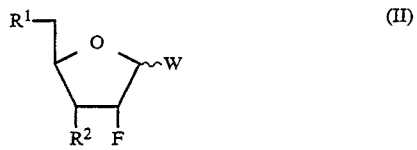

(wherein $R^1$ and $R^2$ are as hereinbefore defined and W is a phosphate ester or salt thereof or a purine or pyrimidine moiety (other than Pu) in the presence of at least one phosphorylase enzyme such as purine nucleoside phosphorylase and thymidine phosphorylase and an inorganic phosphate or a salt thereof, or a transferase enzyme, for example, N-deoxyribosyl transferase. For the purposes of this reaction it is preferred that the purine or pyrimidine moiety be in the $\beta$-position and the phosphate ester or salt thereof in the $\alpha$-position.

The appropriate purine base of formula PuH may be obtained commercially, for example, from Pacific Chemical Laboratories or Sigma Chemical company or prepared by conventional methods well known to a skilled person or readily available from the chemical literature. For example, purine bases where the 2-substituent is amino or hydrogen and the 6-substituent is amino or methylthio may be obtained commercially. Purines where the 2-substituent is amino and the 6-substituent is a methylamino group may be prepared according to the method of Montgomery and Holum (J.A.C.S. 80:404, 1958). Purines in which the 2-substituent is amino and the 6-substituent is alkoxy, for example, methoxy, may be prepared by the method described by Balsiger and Montgomery (J. Org. Chem. 20:1573, 1960).

Compounds of formula (II) may be prepared by methods well known to a skilled person or readily available from the chemical literature. For example, 1-(2-deoxy-2-fluoro-$\beta$-D-ribofuranosyl)uracil may be prepared by the method described in Codington et al. (J. Org. Chem 29:558, 1964). 9-(2-deoxy-2-fluoro-$\beta$-D ribofuranosyl)adenine may be prepared by the method described by S. Uesugi et al (Nucleosides and Nucleotides 2, 373-, 1983).

With regard to process (B), which is particularly suitable for the preparation of compounds of formula (I) from compounds of formula (III) wherein $R^{1a}$ and $R^{2a}$ are both hydroxy, the protected groups $X^a$, $Y^a$, $R^{1a}$ and $R^{2a}$ of compounds of formula (III) may be protected with conventional hydroxy and amino protecting groups such as acyl groups, for example, alkanoyl such as benzoyl, or aroyl groups such as acetyl; aralkyl groups for example a benzyl group; or trialkylsilyl groups such as tert-butyldimethylsilyl, the particular type of protecting group employed being dependent on the nature of the group to be protected.

The protecting group can subsequently be removed by acid or base hydrolysis, hydrogenolysis or enzymatically. Acyl groups are typically removed by base hydrolysis and silyl groups by acid hydrolysis or fluoride ion. Aralkyl groups such as benzyl are advantageously removed by catalytic hydrogenolysis, typically in the presence of a catalyst such as palladium on charcoal or reductively, for example, with an alkali metal (e.g. sodium) in a suitable solvent such as liquid ammonia. It has been found that the use of a benzyl protecting group is particularly advantageous for the preparation of compounds of formula (I) wherein X is hydroxy or amino.

For the preparation of a compound of formula (I) in which $R^1$ and/or $R^2$ represents a group $OCOCHR^9NR^{10}R^{11}$, in accordance with process (B) the groups $R^{1a}$ and/or $R^{2a}$ may be protected with, for example, 9-fluorenylmethyloxy carbonyl (FMOC), tert-butyloxycarbonyl (tBOC) or carbobenzyloxy (CBZ) and may be deprotected by conventional means to give the amino acid $CHR^9NR^{10}R^{11}$.

The starting compound of formula (III) may conveniently be prepared by reacting an appropriate purine base of formula (IV)

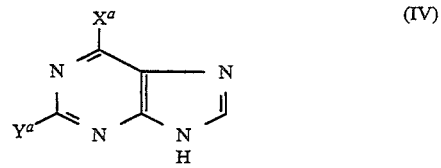

wherein $X^a$ and $Y^a$ are as hereinbefore defined; or a salt thereof, with a pyrimidine nucleoside containing the appropriate sugar residue, for example, 1-(2-deoxy-2-fluoro-$\beta$-D-ribofuranosyl)uracil in the presence of one or more phosphorylase enzymes, for example, purine nucleoside phosphorylase and thymidine phosphorylase, or a transferase enzyme, for example N-deoxyribosyl transferase.

Alternatively a starting compound of formula (III) above can be prepared chemically by reacting a compound of formula (IV) wherein $X^a$ and $Y^a$ are as hereinbefore defined, or a silylated derivative thereof, or a salt thereof, with a compound of formula (II) wherein $R^1$ and $R^2$ are as hereinbefore defined or other protected forms of hydroxy and W is a suitable leaving group, for example, a halogen atom, such as chlorine, an acyloxy group such as acetoxy, an alkoxy group such as methoxy, in the presence of a catalyst such as tin (IV) chloride or trimethylsilyl triflate in a suitable solvent such as acetonitrile.

Purine bases of formula (IV) may be prepared from a corresponding purine base wherein the 6-substituent is a suitable leaving group, for example, a halogen atom, such as chlorine, by nucleophilic displacement of said group. Thus a purine base of formula (IV) wherein $X^a$ is benzyloxy may be prepared for example, by treatment of the corresponding 6-chloro purine with an alcohol such as benzyl alcohol in the presence of a base, for example, sodium hydride in a suitable solvent such as tetrahydrofuran (THF). Purine bases of formula (IV) wherein $X^a$ is benzylamino may be prepared by treatment of the corresponding 6-chloropurine with an amine, for example benzylamine in the presence of a base, for example, an amine such as triethylamine in a suitable solvent such as methanol. Such purine bases used as the above starting materials may be obtained commercially (Aldrich Chemical Company) or prepared by methods well known to a skilled person or readily available from the chemical literature.

Pyrimidine nucleosides employed in the above preparation of the compounds of formula (III) may be prepared by methods well known to a skilled man or readily available from the chemical literature. For example, 1-(2-deoxy-2-fluoro-$\beta$-D-ribofuranosyl)pyrimidines, such as 1-(2-deoxy-2-fluoro-$\beta$-D-ribofuranosyl)uracil, may be prepared by the method described in Codington et al (J. Org. Chem. 29:558, 1964).

It will be appreciated that compounds of formula (III) may represent compounds according to the invention thus, for example, $X^a$ may represent $—NR^3R^4$ where $R^3$ and $R^4$ are as hereinbefore defined. Such compounds may be treated with a deaminase enzyme such as adenosine deaminase and converted to a compound of formula (I) where X is hydroxy.

A compound of formula (I), wherein $R^1$ and/or $R^2$ are hydroxy may be converted into a corresponding pharmaceutically acceptable ester of formula (I) as hereinbefore defined, by reaction with an appropriate esterifying agent according to methods known in the art, for example, by the method described by Martin et al, J. Pharm. Sci. (1987) 76, 180-). Thus, for the preparation of appropriate carboxylic acid esters as defined above the former compound of formula (I) may be reacted with an acid anhydride or acid halide, for example, chloride corresponding to a carboxylic acid of the formula, QCOOH where Q is a group $—R^6H$, $—OR^7H$, $—R^6COOR^8$, $—R^7—Z—Ar$, $—CHR^9NR^{10}R^{11}$ or $—R^{13}$ where $R^6$, $R^7$, $R^8$, $R^9$, $R^{10}$, $R^{11}$, $R^{13}$, Z and Ar are as defined above, in the presence of a suitable base such as triethylamine. Alternatively, the acid QCOOH may be reacted with a compound of formula (I) wherein $R^1$ and/or $R^2$ are hydroxy in the presence of a coupling agent such as dicyclohexylcarbodiimide.

The above starting material of formula (II) wherein $R^1$ and/or $R^2$ are hydroxy may be reacted with an esterifying agent and the resulting compound reacted with the purine base of formula PuH in accordance with process (A).

Compounds according to the invention when $R^1$ and/or $R^2$ are mono-, di- or tri-phosphate esters may be prepared from compounds of formula (I) when $R^1$ and/or $R^2$ are hydroxy by successive phosphorylation via the mono-, di- and tri-phosphate derivatives by conventional chemical means or by enzymatic means, for example using a nucleoside kinase or phosphotransferase in the presence of a nucleotide triphosphate, for example ATP.

A compound of formula (I) wherein $R^1$ and/or $R^2$ are hydroxy may be converted into a corresponding pharmaceutically acceptable ether of formula (I), as hereinbefore defined, by reaction with an appropriate alkylating agent in a conventional manner, for example, a compound of formula $Q^1$—Hal wherein $Q^1$ is a group $—R^6H$ or $—R^6—Z—Ar$ where $R^6$ and Ar are as hereinbefore defined and Hal is a halogen, e.g. iodine.

Alternatively, such an alkylating agent can be reacted with a sugar of formula

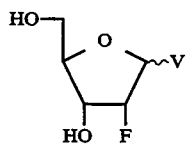

(wherein V is an alkoxy group such as methoxy, or an acyloxy group, such as acetoxy) to obtain a corresponding 3'-, 5'- or 3',5'-di-ether, (Bessodes M et al, Synthesis (1988)560) and condensing the resulting ether with a suitable purine base of formula PuH to form a nucleoside which is then deprotected in accordance with process (B) above.

Where the product obtained from the first step of the above process is a mono-ether, for example a 5'-ether, the other hydroxy group may be reacted with a carboxylic acid or derivative thereof, e.g. an acid anhydride or acid halide, e.g. chloride corresponding to a carboxylic acid of formula QCOOH where Q is as defined above, to obtain a mono-ether-mono-ester sugar, e.g. a 3'-ester-5'-ether sugar. This sugar can be condensed with a suitable purine to form a nucleoside as mentioned above, or by reference to Codington J. F. et al, Carbohyd. Res. (1966) 1,455.

Compounds according to the invention may also be obtained from compounds of the formula I', where I' is a compound corresponding to the compound of formula (I) in which the groups $R^1$ and $R^2$ are replaced by other protecting groups. These other protecting groups may be removed or reacted to produce the groups $R^1$ and $R^2$ as defined above.

Compounds according to the invention, when produced by the route described above, can be used to obtain compounds of the invention when $R^1$ and/or $R^2$ are hydroxy by deprotecting the ether and/or ester groups.

Depending on the process conditions and the starting materials, the end product of the formula (I) is obtained either as the free base or as a salt. Both the free base and the salts of the end products are included within the scope of the invention. Thus, basic, neutral or mixed salts may be obtained as well as hemi-, mono-, sesqui- or poly-hydrates. Acid addition salts of the new compounds may in a manner known per se be transformed into free base using basic agents such as alkali or by ion exchange. The free bases obtained may also form salts with organic or inorganic acids.

Salts according to the invention which may be conveniently used in therapy include pharmaceutically acceptable base salts, eg derived from an appropriate base, such as alkali metal (e.g. sodium), alkaline earth metal (e.g. magnesium) salts, ammonium and $NX_4$ (wherein X is $C_{1-4}$ alkyl) salts.

The present invention further includes the novel intermediates: 2-amino-6-benzylamino-(2-deoxy-2-fluoro-$\beta$-D-ribofuranosyl)-9H-purine, 2-amino-6-benzyloxy-(2-deoxy-2-fluoro-$\beta$-D-ribofuranosyl)-9H-purine, and 2-amino-6-benzylthio-(2-deoxy-2-fluoro-$\beta$-D-ribofuranosyl)-9H-purine.

The compounds according to the invention may be administered to recipients such as mammals including humans by any route appropriate to the condition to be treated, suitable routes including oral, pulmonic, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

The amount required of the individual active ingredient for the treatment of a viral infection including influenza and RSV infections will depend upon a number of factors including the severity of the condition to be treated and the identity of the recipient and will ultimately be at the discretion of the attendant physician. In general, a suitable, effective dose will be in the range 0.1 to 100 mg per kilogram body weight of recipient per day, preferably in the range 5 to 30 mg per kilogram body weight per day and most preferably in the range 10 to 20 mg per kilogram body weight per day; an optimum dose is about 15 mg per kilogram body weight per day (unless otherwise indicated all weights of active ingredient are calculated as the parent compound; for salts and esters thereof the figures would be increased proportionately.) The effective dose may optionally be presented as two, three, four or more sub-doses administered at appropriate intervals throughout the day. These sub-doses may be administered in unit dosage forms, for example, containing 1 to 2000 mg preferably 20 to 500 mg and most preferably 100 to 400 mg of active ingredient per unit dosage form. A suitable effective antiprotozoal dose, e.g., for treatment of *Trichomonas vaginalis* and *Giardia lamblia* infection will be in the range of 10 to 150 mg per kilogram body weight of the mammal per day, preferably in the range of 25 to 75 mg per kilogram body weight per day.

The compounds according to the present invention may be administered alone or in combination with other therapeutic agents, for example, with amantidine or with ribavirin, which are known anti-influenza agents, or an analgesic, for example, codeine, paracetamol, aspirin, ibuprofen or an anti-inflammatory agent, such as, indomethacin, mefenamic acid, naproxen, or ibuprofen or any other agents which when in combination with a compound according to the invention provide a beneficial therapeutic effect.

While it is possible for the compounds to be administered alone it is preferable to present them as pharmaceutical formulations. The formulations according to the present invention comprise at least one active ingredient, as above defined, together with one or more pharmaceutically acceptable carriers therefor and optionally other therapeutic ingredients. The carrier(s) must be "acceptable" in the sense of being compatible with the other ingredients of the formulation and not deleterious to the recipients thereof.

The formulations include those suitable for oral, pulmonic, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations according to the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, or paste or may be contained within liposomes.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropyl- methyl cellulose), lubricant, inert diluent, preservative, disintegrant (e.g. sodium starch glycolate, cross-linked povidone, cross-linked sodium carboxymethyl cellulose), surface-active or dispersing agent. Molding tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxpropylmethylcellulose in varying proportions to provide the desired release profile.

A capsule may be made by filling a loose or compressed powder on an appropriate filling machine, optionally with one or more additives. Examples of suitable additives include binders such as povidone, gelatin, lubricants, inert diluents, distintegrants as for tablets. Capsules may also be formulated to contain pellets or discrete sub-units to provide slow or controlled release of the outline ingredient. This can be achieved by extruding and spheronising a wet mixture of the drug plus an extrusion aid (e.g. microcrystalline cellulose) plus a diluent such as lactose. The spheroids thus produced can be coated with a semi-permeable membrane (e.g. ethyl cellulose, Eudragit WE30D) to produce sustained release properties.

For topical administration the formulations are preferably applied as an ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as in a water in oil base.

If desired, the aqueous phase of the cream base may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glycerol mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, ispropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oil can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or higher fatty alcohol (e.g. hard wax European Pharmacopoeia) or triglycerides and saturated fatty acids (e.g. Witepsol).

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Suitable formulations for administration by inhalation include fine particle dusts or mists which may be generated by means of various types of metered dose pressurised aerosols, nebulizers or insufflators.

For pulmonary administration via the mouth, the particle size of the powder or droplets is typically in the range 0.5–10 μm, preferably 1–5 μm, to ensure delivery into the bronchial tree. For nasal administration, a particle size in the range 10–500 μm is preferred to ensure retention in the nasal cavity.

Metered dose inhalers are pressurised aerosol dispensers, typically containing a suspension or solution formulation of the active ingredient in liquefied propellant. During use these devices discharge the formulation through a valve adapted to deliver a metered volume, typically from 10–150 μl, to produce a fine particle spray containing the active ingredient. Suitable propellants include propane and butane, certain chlorofluorocarbon compounds, commonly referred to as "CFS's", for example, dichlorodifluoromethane, trichlorofluoromethane, dichlorotetrafluoromethane, or mixtures thereof. The formulation may additionally contain co-solvents, for example ethanol, surfactants such as oleic acid or sorbitan trioleate, antioxidants and/or suitable flavouring agents.

Nebulizers are commercially available devices that transform solutions or suspensions of the active ingredient into an aerosol therapeutic mist either by means of acceleration of a compressed gas through a narrow venturi orifice, typically air or oxygen, or by means of ultrasonic agitation. Suitable formulations for use in nebulizers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives includes preservatives if the formulation is not prepared sterile, for example methylhydroxybenzoate, antioxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in-situ and the powder either presented to air drawn through the device upon inhalation or alternatively delivered by means of a manually operated pump. The powder employed in the insufflator consists either solely of the active ingredient or of a powder blend comprising the active ingredient, a suitable powder diluent such as lactose, and an optional surfactant. The active ingredient typically comprises from 0.1–100% w/w of the formulation.

Pressurised aerosol formulations for inhalation are preferably arranged so that each metered dose contains from 0.05 to 5 mg of a compound of the invention. Similarly, powder formulations for insufflations are so arranged that each unit dose contains from 0.5 to 50 mg. Solution or suspension formulations for nebulisation are arranged as to deliver doses between 1 and 1500 mg. The compounds according to the invention or formulations thereof may be administered by these devices once or several times daily, with one or several doses, for example three or four, being given on each occasion.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Injection solutions and suspensions may be prepared extemporaneously from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The following Examples are provided by way of illustration of the present invention and should in no way be construed as limitation thereof.

EXAMPLE 1

Preparation of 9-(2-Deoxy-3,5-di-O propionyl-2-fluoro-$\beta$-D-ribofuranosyl)guanine To a solution of 9-(2-deoxy-2-fluoro-$\beta$-D-ribofuranosyl)guanine (170 mg, 0.6 mmol), DMAP (4-dimethylaminopyridine) (8 mg) and triethylamine (0.41 ml, 5 eq.) in DMF (N,N-dimethylformamide) (4 ml) at room temperature was added propionic anhydride (0.16 ml, 2.1 eq) with stirring. After 20 hours, methanol (2 ml) was added. One hour later the mixture was evaporated in vacuo and the residue was chromatographed over $SiO_2$ using the flash technique. Elution was with $CHCl_3$/MeOH (10:1), then (6:1), affording the title compound as a white solid.

mp. 198°–200° C.

Anal. Calc. for 0.2. hydrate: C, 47.93; H, 5.13; N, 17.47 Found: C, 48.22; H, 4.94; N, 17.0

EXAMPLE 2

Preparation of
9-(2-Deoxy-3,5-di-O-acetyl-2-fluoro-$\beta$-D-ribofuranosyl)guanine, and
9-(2-deoxy-2-fluoro-3,5-di-O-acetyl-$\beta$-D-ribofuranosyl)-2-N-acetyl guanine To a solution of 9-(2-deoxy-2-fluoro-$\beta$-D-ribofuranosyl)guanine (160 mg, 0.56 mmol), DMAP (8 mg) and triethylamine (400 $\mu$l, 5 eq.) in DMF (4 ml) was added acetic anhydride (0.16 ml, 2.5 eq) with stirring at room temperature. After 22 hours the yellow solution was evaporated in vacuo, co-evaporated with ethanol and toluene and chromatographed over $SiO_2$ using the flash technique and eluting with $CHCl_3$/MeOH (6:1). The first eluted component was evaporated, and co-evaporated with toluene to afford the triacetyl derivative as a white foam.

Anal. Calc. for 0.1 toluate: C, 47.69; H, 4.51; N, 16.65 Found: C, 47.47; H, 4.37; N, 16.82

Collection and evaporation of fractions containing the second eluted compound gave the di-acetyl derivative as a white solid.

mp. 232°–234° C. (dec.)

Anal. Calc. for 0.25 ethanolate: C, 45.73; H, 4.63; N, 18.39 C, 46.02; H, 4.34; N, 18.19

EXAMPLE 3

Preparation of
9-(2-Deoxy-2-fluoro-3-O-pivaloyl-$\beta$-D-ribofuranosyl)guanine, and
9-(2-Deoxy-2-fluoro-3,5-di-O-pivaloyl-$\beta$-D-ribofuranosyl)guanine To a solution of 9-(2-deoxy-2-fluoro-$\beta$-D-ribofuranosyl)guanine (200 mg), 0.70 mmol), DMAP (10 mg) and triethylamine (0.5 ml) in DMF (6 ml) at room temperature was added trimethylacetic anhydride (160 $\mu$l, 1.1 eq) and the solution stirred for 24 hours. A further 80 $\mu$l trimethylacetic anhydride was then added and stirring continued for five days. The reaction was quenched with methanol (1 ml), evaporated under reduced pressure to a white solid, and chromatographed over $SiO_2$ using the flash technique, eluting with $CHCl_3$/MeOH (15:1), then (10:1), (6:1), and finally (4:1).

The third eluted UV absorbing fraction was the 3',5'-bis pivalate ester as a waxy solid after trituration with ether.

mp. 250°–252° C. (dec).

Anal. $C_{20}H_{28}FN_5O_6 \cdot 0.5H_2O$ requires: C, 51.94; H, 6.32; N, 15.15 Found: C, 51.99; H, 6.23; N, 14.83

The fourth eluted UV absorbing fraction was the 3'-pivalate ester as a white powder. mp. gradually darkens from 260°–320° C.

Anal. $C_{15}H_{20}FN_5O_5$ 0.7$H_2O$ requires: C, 47.17; H, 5.65; N, 18.34 Found: C, 47.10; H, 5.36; N, 17.93

EXAMPLE 4

Preparation of
9-(2-Deoxy-2-fluoro-3,5-di-O-pivaloyl-$\beta$-D-ribofuranosyl)adenine,
9-(2-Deoxy-2-fluoro-3-O-pivaloyl-$\beta$-D-ribofuranosyl)adenine and
9-(2-Deoxy-2-fluoro-5-O-pivaloyl-$\beta$-D-ribofuranosyl)adenine To a solution of 9-(2-deoxy-2-fluoro-$\beta$-D-ribofuranosyl)adenine (250 mg, 0.93 mmol) DMAP (10 mg) and triethylamine (0.65 ml) in dry DMF (7 ml) was added trimethylacetic anhydride (226 $\mu$l, 1.2 eq) at room temperature with stirring. After 24 hours a further 60 $\mu$l trimethylacetic anhydride was added, followed 24 hours later by a further 20 $\mu$l. After one further day the reaction was quenched with MeOH, evaporated in vacuo, co-evaporated with ethanol and purified by flash chromatography over $SiO_2$. Elution was with $CHCL_3$/MeOH (18:1), (15:1) and finally (10:1). The first eluted UV absorbing fraction was the 3'5'-bis ester as a white solid after trituration with ether.

mp. 157°–158° C.

Anal. $C_{20}H_{28}FN_5O_5 \cdot 0.3H_2O$ requires: C, 54.24; H, 6.51; N, 15.82 Found: C, 54.40; H. 6.33; N, 15.48

The second eluted UV absorbing fraction was the 3'-pivalate ester as a white solid.

mp. 204°–205° C.

Anal. for $C_{15}H_{20}FN_5O_4 \cdot 0.3H_2O$ requires: C, 50.22; H, 5.79; N, 19.53 Found: C, 50.25; H, 5.58; N, 19.31

The third eluted UV absorbing fraction was the 5'-pivalate ester as a white foam.

mp. 130°–134° C.

Anal. $C_{15}H_{20}FN_5O_4 \cdot 0.2H_2O$ requires: C, 50.46; H, 5.76; N, 19.62 Found: C, 50.57; H, 5.65; N, 19.45

EXAMPLE 5

Preparation of
9(2-Deoxy-2-fluoro-3,5-di-O-valeryl-$\beta$-D-ribofuranosyl)adenine,
9(2-Deoxy-2-fluoro-3-O-valeryl-$\beta$-D-ribofuranosyl)adenine and
9(2-Deoxy-2-fluoro-5-O-valeryl-$\beta$-D-ribofuranosyl)adenine To a solution of 9-(2-deoxy-2-fluoro-$\beta$-D-ribofuranosyl)adenine (300 mg, 1.11 mmol) DMAP (10 mg) and triethylamine (0.9 ml) in dry DMF (8 ml) was added valeric anhydride (263 μl, 1.2 eq) at room temperature with stirring. At 24 and 48 hours a further 30 μl valeric anhydride was added. One day after the final addition the mixture was quenched with MeOH, and then worked up and chromatographed as for the preparation of the pivalate esters. The first eluted UV absorbing component was the 3',5'-bis ester, which crystallised as white needles upon trituration with ether.

mp. 96°–98° C.

Anal. $C_{20}H_{28}FN_5O_5$ requires: C, 54.91; H, 6.45; N, 16.01 Found: C, 54.93; H, 6.49; N, 15.89

The second eluted UV absorbing component was the 3'-valerate ester.

mp. 182°–183° C.

Anal. $C_{15}H_{20}FN_5O_4$ requires: C, 50.98; H, 5.71; N, 19.82 Found: C, 50.91; H, 5.82; N, 19.46

The third eluted UV absorbing component was the 5'-valerate ester, which crystallised upon trituration with ether.

mp. 115°–117° C.

Anal. $C_{15}H_{20}FN_5O_4$ requires: C, 50.98; H, 5.71; N, 19.82 Found C, 50.76; H, 5.81; N, 19.44

EXAMPLE 6

2,6-Diamino-9-(2-deoxy-2-fluoro-β-D-ribofuranosyl)-9H-purine 2,6-Diaminopurine (Pacific Chemical Laboratories, 0.8 g, 4.8 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 50 ml of 5 mM potassium phosphate buffer, pH 7.0, which contained 0.04% (w/w) potassium azide. Thymidine phosphorylase (3,850 I.U.) and purine nucleoside phosphorylase (3,760 I.U.) (T. A. Krenitsky et al., Biochemistry 20:3615, 1981 and U.S. Pat. No. 4,381,344) were added and the suspension stirred at 37° C. On day 12, the reaction was filtered. The filtrate was applied to a 1.5×15 cm column of anion exchange resin (Bio-Rad AG1X2-hydroxide form). After washing the column with water/methanol (7/3), the product was eluted with water/methanol (1/1). Product containing fractions were combined and the solvent removed under vacuum. The residue was dissolved in water and lyophilized to obtain title compound that analyzed as a 1.2 hydrate.

mp. 124° C. UV λmax nm ($\epsilon \times 10^{-3}$): 0.1N HCl, 291 (10.2), 252 (11.8); pH 7, 278.5 (10.3), 255 (9.69); 0.1N NaOH, 279 (10.6), 255 (9.69).

Anal. Calcd. for $C_{10}H_{13}FN_6O_3 \cdot 1.2$ $H_2O$: Calcd.: C, 39.27; H, 5.07; N, 27.48; F, 6.21. Found: C, 39.22; H, 5.09; N, 27.39; F, 6.45.

$^1$H-NMR (80 mHz, $Me_2SO$-d6): δ 7.94 (s, 1H, H-8); 6.74 and 5.79 (2 bs, 4H, 2-NH2 and 6-NH2); 6.04 (dd, 1H, H-1', JF,1'=16.5 Hz, J=3.4 Hz); 5.64 (m, 1.5H, 0.5 (H-2') and 3'-OH); 5.25 (t, 1H, 5'-OH, J=5.5 Hz); 4.98 (m, 0.5H, 0.5 (H-2')); 4.41 (m, 1H, H-3'); 3.93 (m, 1H, H-4'); 3.65 (m, 2H, $H_\alpha$-5' and $H_\beta$-5').

EXAMPLE 7

9-(2-Deoxy-2-fluoro-β-D-ribofuranosyl)guanine 2,6-Diamino-9-(2-deoxy-2-fluoro-β-D-ribofuranosyl)-9H-purine (0.20 g, 0.64 mmole), prepared as in Example 6, was dissolved in 15 ml of water. Calf intestinal adenosine deaminase (4 I.U., Boehringer Mannheim) was added and the solution incubated at 37° for 4 days. The solution was cooled to 4° C. After 3 hrs, the suspension was filtered to remove the first batch of product crystals. The volume of the filtrate was reduced under vacuum and the suspension cooled to 4° C. The suspension was filtered to remove the second batch of product crystals. The batches of product crystals were combined, suspended in water and lyophilized to obtain title compound that analyzed as a 1.3 hydrate.

mp. >250° C. (dec.)

UV λmax nm ($\epsilon \times 10^{-3}$): 0.1N HCl, 257 (12.2), 280 (sh); 0.1N NaOH, 257–264 (10.9).

Anal. Calcd. for $C_{10}H_{12}FN_5O_4 \cdot 1.3$ $H_2O$: Calcd.: C, 38.91; H, 4.77; N, 22.69; F, 6.16. Found: C, 38.60; H, 4.82; N, 22.51; F, 6.44.

$^1$H-NMR (80 mHz, $Me_2SO$-d6): δ 10.63 (bs, 1H, N1-H); 7.94 (s, 1H, H-8); 6.51 (bs, 2H, 2-NH2); 6.00 (dd, 1H, H-1', JF,1'=16.5 Hz, J=2.9 Hz); 5.59 (m, 1.5H, 0.5 (H-2') and 3'-OH); 5.10 (t, 1H, 5'-OH, J=5.6 Hz); 4.90 (m, 0.5H, 0.5 (H-2')); 4.37 (m, 1H, H-3'); 3.90 (m, 1H, H-4'); 3.65 (m, 2H, $H_\alpha$-5' and $H_\beta$-5').

EXAMPLE 8

9-(2-Deoxy-2-fluoro-β-D-ribofuranosyl)adenine

Adenine (Mann Research Laboratories, Inc., 0.8 g, 5.9 mmoles) and 1-(2-deoxy-2-fluoro-β-D-ribofuranosyl)uracil (0.4 g; 1.6 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. Thymidine phosphorylase (2,400 I.U.) and purine nucleoside phosphorylase (3,900 I.U.) (T. A. Krenitsky et al., Biochemistry 20:3615, 1981 and U.S. Pat. No. 4,381,344) were added and the suspension stirred at 37° C. On day 6, the reaction was diluted to 100 ml with 5 mM potassium phosphate buffer, pH 7.0, which contained 0.04% (w/v) potassium azide. On day 17, the suspension was filtered and the filtrate was evaporated. The residue was suspended in warm water. The suspension was filtered and the filtrate applied to a 1.5×12 cm column of anion exchange resin (Bio-Rad AG1X2-hydroxide form). The product was eluted with water. Product containing fractions were combined and the solvent removed under vacuum. The residue was dissolved in water and lyophilized to obtain the title compound that analyzed as a 0.6 hydrate.

mp. 225°–227° C. nm (dec.)

UV λmax nm ($\epsilon \times 10^{-3}$): 0.1N HCl, 257 (14.6); 0.1N NaOH, 260 (14.9).

Anal. Calcd. for $C_{10}H_{12}FN_5O_3 \cdot 0.6$ $H_2O$: Calcd.: C, 42.89; H, 4.57; N, 25.01; F, 6.78. Found: C, 42.94; H, 4.76; N, 24.98; F, 6.89.

$^1$H-NMR (250 mHz, $Me_2SO$-d6): δ 8.35 and 8.14 (2s, 2H, H-8 and H-2); 7.36 (s, 2H, 6-NH2); 6.21 (dd, 1H, H-1', JF,1'=16.8 Hz, J=3.0 Hz) 5.71 (d, 1H, 3'-OH, J=6.0 Hz); 5.42 (ddd, 1H, H-2', JF,2'=53.0 Hz, J1',2'=3.0 Hz, J2',3'=4.5 Hz); 5.25 (t, 1H, 5'-OH, J=5.6 Hz); 4.47 (m, 1H, H-3'); 3.97 (m, 1H, H-4'); 3.74 (m, 1H, $H_\alpha$-5'); 3.56 (m, 1H, $H_\beta$-5').

EXAMPLE 9

2-Amino-9-(2-deoxy-2-fluoro-β-D-ribofuranosyl)-9H-purine

2-Aminopurine (Vega Biochemicals, 0.4 g, 3.0 mmoles) and 1-(2-deoxy-2-fluoro-β-D-ribofuranosyl)uracil (0.2 g, 0.71 mmoles) which may be prepared according to J. F. Codington et al. (J. Org. Chem. 29:558, 1964) were suspended in 35 ml of 5 mM potassium phosphate buffer, pH 7.0, which contained 0.04% (w/v) potassium azide. Thymidine phosphorylase (1,930 I.U.) and purine nucleoside phosphorylase (1,880 I.U.) (T. A. Krenitsky et al., Biochemistry 20:3615, 1981 and U.S. Pat. No. 4,381,344) were added and the suspension stirred at 37° C. On day 24, the reaction was diluted to 200 ml with water and 1,390 I.U. of thymidine phosphorylase, and, 1,880 I.U. of purine nucleoside phosphorylase were added. On day 35, the suspension was evaporated. The residue was dissolved in water/methanol (7/3) and applied to a 1.5×15 cm column of anion exchange resin (Bio-Rad AG1X2-hydroxide form). The product was eluted with water/methanol (7/3). The product-containing fractions were combined and the solvent removed under vacuum. The residue was dissolved in water and lyophilized to obtain title compound that analyzed as a 0.6 hydrate.

mp. 151°–153° C.

UV λmax nm ($\epsilon \times 10^{-3}$): 0.1N HCl, 313 (4.00), 240–245; pH 7, 304 (7.00), 243; 0.1N NaOH, 304 (7.30), 243.

Anal. Calcd. for $C_{10}H_{12}FN_5O_3$ 0.6 $H_2O$. Calcd.: C, 42.89; H, 4.75; N, 25.01; F, 6.78. Found: C, 43.02; H, 4.71; N, 25.12; F, 6.58

$^1$H-NMR (80 mHz, Me$_2$SO-d$_6$): δ 8.62 and 8.31 (2s, 2H, H-8 and H-6); 6.62 (bs, 2H, 2-NH2); 6.16 (dd, 1H, H-1', JF,1'=16.7 Hz, J=2.7 Hz); 5.71 (m, 1.5H, 3'-OH and 0.5 (H-2')); 5.12 (m, 1.5H, 5'-OH and 0.5 (H-2')); 4.40 (m, 1H, H-3'); 3.97 (m, 1H, H-4'); 3.66 (m, 2H, H$_\alpha$-5' and H$_\beta$-5').

EXAMPLE 10

2-Amino-6-cyclopropylamino-9H-purine-hydrochloride

A solution of 2-amino-6-chloro-purine (Aldrich Chemical Company, 4.66 g, 27.5 mmoles) and cyclopropylamine (Aldrich Chemical Company, 12.5 g, 220 mmoles) in MeOH (100 ml) was heated at 50° C. for 18 hours. Then 2-methoxyethanol (50 ml) was added, and the reaction was heated at 70° C. for an additional 6 hours. After cooling, a small amount of unreacted starting material was filtered off, and the filtrate was evaporated and purified on a silica gel column with CHCl$_3$: 5% to 10% MeOH. The product was then recrystallized twice from MeOH and once from EtOH as a hydrochloride salt to give 1.45 g (23%) of product; mp. 253°–257° C.

$^1$H-NMR (Me$_2$SO-d$_6$): δ 6.70–6.82 (m, 4, CH$_2$CH$_2$), 3.04 (br, s, 1, CHN), 7.35–7.55 (br, s, 2, NH$_2$), 8.13 (s, 1, CH), 9.49 (br s, 1, NHCH), 13.0–13.3 (br, s, 2, NH$_2$+).

Anal. Calcd. for $C_8H_{10}N_6$·HCl·1..H$_2$O: Calcd.: C, 41.57; H, 5.01; N, 36.35; Cl, 15.34. Found: C, 41.55; H, 5.01; N, 36.28; Cl, 15.4.

2-Amino-6-(cyclopropylamino)-9-(2-deoxy-2-fluoro-β-D-ribofuranosyl)-9H-purine

2-Amino-6-(cyclopropylamino)-9H-purine hydrochloride (0.3 g, 1.3 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were dissolved in 20 ml of 5 mM potassium phosphate buffer, pH 7.0, which contained 0.04% (w/v) potassium azide. Thymidine phosphorylase (2,000 I.U.) and purine nucleoside phosphorylase (5,540 I.U.) (T. A. Krenitsky et al., Biochemistry 20:3615, 1981 and U.S. Pat. No. 4,381,444) were added and the reaction incubated at 37° C. On day 5, 2,000 I.U. thymidine phosphorylase and 5,540 I.U. purine nucleoside phosphorylase were added. On day 21, the reaction was applied to a 2.5×8 cm column of anion exchange resin (Bio-Rad AG1X2-hydroxide form). After washing the column with water, the product was eluted with water/methanol (7/3). The product-containing fractions were combined and the solvent removed under vacuum. The residue was dissolved in water and lyophilized to obtain title compound that analyzed as a 0.6 hydrate.

mp. 120° C. (Partial melt at 80°).

UV λmax nm ($\epsilon \times 10^{-3}$): 0.1N HCl, 295.5 (14.3), 254 (12.7); pH 7, 282 (14.8) 262 (sh); 0.1N NaOH, 282 (15.2), 262 (sh).

Anal. Calcd. for $C_{13}H_{17}FN_6O_3$·0.6 $H_2O$: Calcd.: C, 46.59; H, 5.47; N, 25.08; F, 5.67. Found: C, 46.46; H, 5.35; N, 25.03; F, 5.91.

$^1$H-NMR (200 mHz, Me$_2$SO-d$_6$): δ 7.93 (s, 1H, H-8); 7.38 (bd, 1H, 6-NH, J=4.5 Hz); 6.04 (dd, 1H, H-1', JF,1=16.4 Hz, J=3.3 Hz); 5.88 (bs, 2H, 2-NH); 5.62 (d, 1H, 3'-OH, J=5.9 Hz); 5.30 (apparent dt, 1H, H-2', JF,2 53.7 Hz, J 3.8 Hz); 5.23 (t, 1H, 5'-OH, J=5.4 Hz); 4.38 (m, 1H, H-3'); 3.92 (m, 1H, H-4'); 3.69 (m, 1H, H$_\alpha$-5'); 3.59 (m, 1H, H$_\beta$-5'); 3.10 (m, 1H, N-CH); 0.62 (m, 4H, CH2CH2).

EXAMPLE 11

9-(2-Deoxy-2-fluoro-β-D-ribofuranosyl)-6-methoxy-9H-purine

6-Methoxypurine (Sigma Chemical Company; 0.8 g, 5.3 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. Thymidine phosphorylase (2,400 I.U.) and purine nucleoside phosphorylase (3,900 I.U.) (T. A. Krenitsky et al., Biochemistry 20:3615, 1981 and U.S. Pat. No. 4,381,344) were added and the suspension stirred at 37° C. On day 6 the reaction was diluted to 100 ml with 5 mM potassium phosphate buffer, pH 7.0, which contained 0.04% (w/v) potassium azide. On day 16, 2,640 I.U. thymidine phosphorylase and 4,360 I.U. purine nucleoside phosphorylase were added. On day 45, the reaction was evaporated. The residue was suspended in warm methanol and the suspension was filtered. The filtrate was evaporated. The residue was dissolved in warm water and applied to a 2.5×7 cm column of anion exchange resin (Bio-Rad AG1X2-hydroxide form). After washing with water, the product was eluted with methanol/water (9/1). Product-containing fractions were combined and the solvent removed under vacuum. The residue was dissolved in water and lyophilized to obtain title compound which analyzed as a 0.3 hydrate.

mp. 182° C. UV λmax nm ($\epsilon \times 10^{-3}$): 0.1N HCl, 250 (8.72), 259 (sh); pH 7, 248 (8.95), 259 (sh); 0.1N NaOH, 250 (9.14), 259 (sh).

Anal. Calcd. for $C_{11}H_{13}FN_4O_4$·0.3 $H_2O$: Calcd.: C, 45.61; H, 4.73; N, 19.34; F, 6.56. Found: C, 45.72; H, 4.66; N, 19.47; F, 6.72.

$^1$H-NMR (300 mHz, Me$_2$SO-d$_6$): δ 8.63 and 8.58 (2s, 2H, H-8 and H-2); 6.34 (dd, 1H, H-1', JF,1'=17.1 Hz, J=2.4 Hz); 5.76 (d, 1H, 3'-OH, J=6.1 Hz); 5.45 (ddd, 1H, H-2', JF,2'=52.7 Hz, J1',2'=2.4 Hz, J2',3'=4.4 Hz); 5.17 (t, 1H, 5'-OH, J=4.1 Hz); 4.50 (m, 1H, H-3'); 4.11 (s, 3H O—CH3); 4.00 (m, 1H, H-4'); 3.75 (m, 1H, H$_\alpha$-5'); 3.62 (m, 1H, H$_\beta$-5').

EXAMPLE 12

2-Amino-9-(2-deoxy-2-fluoro-β-D-ribofuranosyl)-6-methoxy-9H-purine

2-Amino-6-methoxypurine (0.8 g, 4.8 mmoles) which may be prepared according to R. W. Balsiger and J. A. Montgomery (J. Org. Chem. 20:1573, 1960) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. Thymidine phosphorylase (2,400 I.U.) and purine nucleoside phosphorylase (3,900 I.U.) (T. A. Krenitsky et al., Biochemistry 20:3615, 1981 and U.S. Pat. No. 4,381,344) were added and the suspension stirred at 37° C. On day 6, the reaction was diluted to 100 ml with 5 mM potassium phosphate buffer, pH 7.0, which contained 0.04% (w/v) potassium azide. On day 10, the reaction was diluted to 200 ml with 5 mm potassium phosphate buffer, pH 7.0, which contained 0.04% (w/v) potassium azide. On day 16, 2,640 I.U. of thymidine phosphorylase and 4,360 I.U. of purine nucleoside phosphorylase were added. On day 24, the reaction was filtered and the filtrate was evaporated. The residue was suspended in methanol. The suspension was filtered and the filtrate evaporated. The residue was dissolved in water and applied to a 2.5×7 cm column of anion exchange resin (Bio-Rad AG1X2-hydroxide form). After washing the column with water, the product was eluted with methanol/water (9/1). After the solvent was removed under vacuum, the residue was dissolved in water and lyophilized to obtain title compound which analyzed as a 0.5 hydrate.

mp. 200°–202° C. UV λmax nm ($\epsilon \times 10^{-3}$): 0.1N HCl, 288 (7.85), 244.5 (6.43); pH 7, 279.5 (8.09), 248 (8.85); 0.1N NaOH, 280 (8.40), 248.5 (8.59).

Anal. Calcd. for $C_{11}H_{14}FN_5O_4$ 0.5 $H_2O$: Calcd.: C, 42.86; H, 4.90; N, 22.78; F, 6.16 Found: C, 42.81; H, 4.92; N, 22.69; F, 6.29

$^1$H-NMR (300 mHz, $Me_2SO$-d6): δ 8.12 (s, 1H, H-8); 6.57 (bs, 2H, 2-$NH_2$); 6.11 (dd, 1H, H-1', JF,1'=16.6 Hz, J=2.7 Hz); 5.69 (d, 1H, 3'-OH, J=6.10 Hz); 5.31 (ddd, 1H, H-2', JF,2'=53.0 Hz, J1',2'=2.7 Hz, J2',3'=4.4 Hz); 5.17 (t, 1H, 5'OH, J=4.2 Hz); 4.40 (m, 1H, H-3'); 3.95 (m, 4H, H-4' and O—$CH_3$); 3.74 (m 1H, $H_\alpha$-5'); 3.58 (m, 1H, $H_\beta$-5').

EXAMPLE 13

6-Cyclopropylamino-9H-purine

A solution of 6-chloropurine (Aldrich Chemical Company, 4.23 g, 27 mmoles) and cyclopropylamine (Aldrich Chemical Company, 12.5 g, 22 mmoles) in MeOH (100 ml) was heated at 50° C. for 48 hours. The solvent was removed, and the crude product was purified on a silica gel column eluting with $CHCl_3$: 5% MeOH to obtain 5.90 g of a cream solid. This was recrystallized from MeOH to give two crops, 2.69 g and 1.16 g (81.4% total yield); mp. 237–240.

$^1$H-NMR ($Me_2SO$-d6): δ 0.6–071 (m, 4, $CH_2CH_2$), 3.03 (br s, 1, CHNH), 7.73 (d, 1, NH), 8.05 (s, 1, CH), 8.18 (s, 1, CH), 12.7 (br, 1, NH).

Anal. Calcd. $C_8H_9N_5$: C, 54.85; H, 5.18; N, 39.97. Found: C, 54.69; H, 5.22; N, 39.87.

6-(Cyclopropylamino)-9-(2-deoxy-2-fluoro-β-D-ribofuranosyl)-9H-purine 6-(Cyclopropylamino)-9H-purine (0.2 g, 1.1 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 20 ml of 5 mM potassium phosphate buffer, pH 7.0, which contained 0.04% (w/v) potassium azide. The pH of the suspension was adjusted to 7.0 with KOH. Thymidine phosphorylase (2,000 I.U.) and purine nucleoside phosphorylase (5,540 I.U.) (T. A. Krenitsky et al., Biochemistry 20:3615, 1981 and U.S. Pat. No. 4,381,344) were added and the suspension stirred at 37° C. On day 5, 0.2 g of 6-(cyclopropylamino)purine and 2,000 I.U. of thymidine phosphorylase and 5,540 I.U. of purine nucleoside phosphorylase were added. On day 9, 0.2 g of 6 (cyclopropylamino) purine was added and the pH of the reaction was adjusted to 7.0 with KOH. Thymidine phosphorylase (2,000 I.U.) and purine nucleoside phosphorylase (5,540 I.U.) were added. On day 20, the pH of the reaction was adjusted to 9.4 with $NH_4OH$ and the reaction was applied to a 2.5×8.5 cm column of anion exchange resin (Bio-Rad AG1X2-hydroxide form). After washing with water, the product was eluted with water/methanol (7/3). Product-containing fractions were combined and the solvent removed under vacuum. The residue was dissolved in water and lyophilized to obtain title compound that analyzed as a 0.4 hydrate.

mp. 207°–208° C. UV λmax nm ($\epsilon \times 10^{-3}$): 0.1N HCl, 264 (19.1); pH 7, 268 (18.2); 0.1N NaOH, 268 (18.6).

Anal. Calcd. for $C_{13}H_{16}FN_5O_3$.0.4 $H_2O$: Calcd.: C, 49.33; H, 5.35; N, 22.13; F, 6.00. Found: C, 49.33; H, 5.33; N, 22.11; F, 6.14.

$^1$H-NMR (200 mHz, $Me_2SO$-d6): δ 8.35 and 8.24 (2s, 2H, H-8 and H-2); 7.98 (bd, 1H, 6-NH, J=4.10 Hz), 6.23 (dd, 1H, H-1', JF,1'=16.8 Hz, J=2.9 Hz); 5.68 (d, 1H, 3'-OH, J=5.9 Hz); 5.42 (ddd, 1H, H-2', JF,2'=53.0 Hz, J1',2'=2.9 Hz, J2',3'=4.6 Hz); 5.20 (t, 1H, 5-OH, J=5.6 Hz); 4.46 (m, 1H, H-3'); 3.97 (m, 1H, H-4'); 3.73 (m, 1H, $H_\alpha$-5'); 3.55 (m, 1H, $H_\beta$-5'); 3.04 (m, 1H, N-CH); 0.66 (m, 4H, $CH_2CH_2$).

EXAMPLE 14

2-Amino-9-(2-deoxy-2-fluoro-β-D-ribofuranosyl)-6-ethoxy-9H-purine

2-Amino-6-ethoxypurine (0.8 g, 4.5 mmoles) which may be prepared according to R. W. Balsiger and J. A. Montgomery (J. Org. Chem. 25:1573, 1960) and 1-(2-deoxy-2-fluoro-β-D-ribofuranosyl)uracil (0.5 g, 2.1 mmoles) which may be prepared according to J. F. Codington et al. (J. Org. Chem. 29:558, 1964) were suspended in 50 ml of 5 mM potassium phosphate buffer, pH 7.0, which contained 0.04% (w/v) potassium azide. The pH of the suspension was adjusted to 7.0 with KOH. Thymidine phosphorylase (4,000 I.U.) and purine nucleoside phosphorylase (14,000 I.U.) (T. A. Krenitsky et al., Biochemistry 20:3615, 1981 and U.S. Pat. No. 4,381,344) were added and the reaction stirred at 37° C. On day 4, 2,000 I.U. of thymidine phosphorylase and 6,980 I.U. of purine nucleoside phosphorylase were added and the reaction was diluted to 250 ml with 5 mM potassium phosphate buffer, pH 7.0, which contained 0.04% (w/v) potassium azide. On day 14, the solvent was removed under vacuum. The residue was suspended in water and methanol added to precipitate the protein. After the suspension was filtered, the filtrate was evaporated. The residue was dissolved in hot water and applied to a 1.5×15 cm column of anion exchange resin (Bio-Rad AG1X2 hydroxide form). After washing the column with water, the product was eluted with methanol/water (1/1). Product-containing fractions were combined and the solvent removed under vacuum. The residue was dissolved in water and lyophilized to obtain title compound that analyzed as 0.7 hydrate.

mp. 85° C. (partial melt at 50° C.) UV λmax nm ($\epsilon \times 10^{-3}$): 0.1N HCl, 288 (8.78), 244.5 (7.19); pH 7, 280 (8.96), 247.5 (9.55); 0.1N NaOH, 280 (9.25), 249 (9.15).

Anal. Calcd. for $C_{12}H_{16}FN_5O_4$ 0.7 $H_2O$: Calcd.: C, 44.23; H, 5.38; N, 21,49; F, 5.83. Found: C, 44.30; H, 5.43; N, 21.39; F, 5.81.

$^1$H-NMR (200 mHz, $Me_2SO$-d6): δ 8.09 (s, 1H, H-8); 6.49 (bs, 2H, 2-NH2); 6.08 (dd, 1H, H-1', JF,1'=16.4 Hz, J=2.7 Hz); 5.67 (d, 1H, 3'-OH, J=6.1 Hz); 5.42 (m, 0.5H, 0.5 (H-2')); 5.15 (m, 1.5H, 0.5 (H-2') and 5'-OH); 4.44 (q, 2H, 6-OCH2, J=7.0 Hz); 4.40 (m, 1H, H-3'); 3.92 (m, 1H, H-4'); 3.73 (m, 1H, H$_\alpha$-5'); 3.56 (m, 1H, H$_\beta$-5'); 1.34 (t, 3H, -CH3, J=7.0 Hz).

EXAMPLE 15

2-Amino-6-chloro-9-(2-deoxy-2-fluoro-β-D-ribofuranosyl)-9H-purine

Reaction 1;

2-Amino-6-chloropurine (Sigma Chemical Company, 0.8 g, 4.7 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 50 ml of 5 mM potassium phosphate buffer, pH 7.0, which contained 0.04% (w/v) potassium azide. The pH of the suspension was adjusted to 7.0 with KOH. Thymidine phosphorylase (3,850 I.U.) and purine nucleoside phosphorylase (6,500 I.U.) (T. A. Krenitsky et al., Biochemistry 20:3615, 1981 and U.S. Pat. No. 4,381,444) were added and the suspension stirred at 37° C. On day 22, the reaction was diluted to 100 ml with 5 mM potassium phosphate buffer, pH 7.0, which contained 0.04% (w/v) potassium azide, and 1,270 I.U. thymidine phosphorylase and 2,180 I.U. purine nucleoside phosphorylase were added. On day 32, the reaction was diluted to 200 ml with 5 mM potassium phosphate buffer, pH 7.0, which contained 0.04% (w/v) potassium azide, and 2,540 I.U. of thymidine phosphorylase and 4,360 I.U. of purine nucleoside phosphorylase were added. On day 61, the reaction was filtered. The filtrate was evaporated and the residue stored at 4°

Reaction 2;

2-Amino-6-chloropurine (Sigma Chemical Company, 0.8 g, 4.7 mmoles) and 1-(2-deoxy-2-fluoro-β-D-ribofuranosyl)uracil (0.4 g, 1.6 mmoles) were suspended in 25 ml of 10 mM potassium phosphate buffer, pH 7.0, which contained 0.04% (w/v) potassium azide. Thymidine phosphorylase (4,000 I.U.) and purine nucleoside phosphorylase (6,500 I.U.) were added and the suspension stirred at 37° C. On day 10, the reaction was diluted to 100 ml with 5 mM potassium phosphate buffer, pH 7.0, which contained 0.04% (w/v) potassium azide. On day 20, the reaction was diluted to 200 ml with 5 mM potassium phosphate buffer, pH 7, which contained 0.04% (w/v) potassium azide, and 2,640 I.U. thymidine phosphorylase and 4,360 I.U. purine nucleoside phosphorylase were added. On day 53, the reaction was filtered. The filtrate was evaporated and the residue stored at 4°. The residues from Reactions 1 and 2 were suspended in water and combined. The suspension was warmed and then filtered. The product which was contained in the filtrate was purified by chromatography on a 7.5×90 cm column of Biogel P-2 (Bio-Rad) with n-propanol/water (3/7) as the solvent, followed by chromatography on a 5×90 cm column of Sephadex G-10 (Pharmacia LKB) with n-propanol/water (3/7) as the solvent. Fractions containing only product were pooled and the solvent removed under vacuum. The residue was suspended in water and lyophilized to obtain the title compound (batch 1). Fractions containing product plus impurities which were eluted off the Sephadex G-10 column were combined and the solvent removed under vacuum. The residue was dissolved in water/MeCN (49/1), and the product was further purified by reversed phase chromatography on C18 silica (Hi-Chrom Prep-40-ODS, Regis Chemical Co.) with water/MeCN (49/1) as the solvent. Product containing fractions were combined and filtered through an 0.2 μm-pore nylon filter to remove residual silica. After the solvent was removed under vacuum, the residue was dissolved in water and filtered through a 0.22 m-pore membrane filter (Millipore GS). Lyophilization of the filtrate yielded the title compound (batch 2) that analyzed as a 0.5 hydrate.

Data for batch 1;

mp. 212° C. (partial melt at 205° C.) UV λmax nm ($\epsilon \times 10^{-3}$): 0.1N HCl, 309 (6.00), 247 (5.60); pH 7, 307.5 (6.30), 247 (5.80); 0.1N NaOH, 307 (6.40), 247 (5.30).

Anal. Calcd. for $C_{10}H_{11}Cl\ FN_5O_3$: Calcd.: C, 39.55; H, 3.65; N, 23.06; Cl, 11.67; F, 6.26. Found: C, 39.69; H, 3.82; N, 22.84; Cl, 11.64; F, 6.14.

$^1$H-NMR (300 mHz, $Me_2SO$-d6): δ 8.37 (s, 1H, H-8); 7.07 (bs, 2H, 2-NH2); 6.12 (dd, 1H, H-1', JF,1'=16.6 Hz, J=2.0 Hz); 5.72 (d, 1H, 3'-OH, J=6.4 Hz); 5.34 (ddd, 1H, H-2', JF,2'=52.9 Hz, J1',2'=2.0 Hz, J2',3'=4.2 Hz); 5.19 (t, 1H, 5'-OH, J=5.3 Hz); 4.42 (m, 1H, H-3'); 3.96 (m, 1H, H-4'); 3.76 (m, 1H, H$_\alpha$-5'); 3.61 (m, 1H, H$_\beta$-5').

Data for batch 2;

mp. 215° C. UV λmax nm: 0.1N HCl, 309.5, 246.5; pH 7, 307.5, 247; 0.1N NaOH, 307.5, 247.

Anal. Calcd. for $C_{10}H_{11}Cl\ FN_5O_3\cdot 0.5\ H_2O$: Calcd.: C, 38.41; H, 3.87; N, 22.40; Cl, 11.34; F, 6.08. Found: C, 38.73; H, 3.79; N, 22.14; Cl, 11.16; F, 6.10.

$^1$H-NMR (80 mHz, $Me_2SO$-d6): 8.36 (s, 1H, H-8); 7.03 (bs, 2H, 2-NH2); 6.13 (dd, 1H, H-1', JF,1' 16.8 Hz, J=3.2 Hz); 5.68 (m, 1.5H, 0.5 (H-2') and 3'-OH); 5.15 (m, 1.5H, 0.5 (H-2') and 5'-OH); 4.35 (m, 1H, H-3'); 3.90 (m, 1H, H-4'); 3.72 (m, 2H, H$_\alpha$-5' and H$_\beta$-5').

EXAMPLE 16

2-Amino-9-(2-deoxy-2-fluoro-β-D-ribofuranosyl)-6-methylamino-9H-purine

2-Amino-6-methylaminopurine (J. A. Montgomery and L. B. Holum, J.A.C.S. 80:404, 1958; 0.51 g; 3.1 mmoles) and 1-(2-deoxy-2-fluoro-β-D-ribofuranosyl)uracil (0.52 g, 2.1 mmoles) which may be prepared according to J. F. Codington et al. (J. Org. Chem. 29:558, 1964) were suspended in 50 ml of 5 mM potassium phosphate buffer, pH 7.0, which contained 0.04% (w/v) potassium azide. Thymidine phosphorylase (4,000 I.U.) and purine nucleoside phosphorylase (14,000 I.U.) (T. A. Krenitsky et al., Biochemistry 20:3615, 1981 and U.S. Pat. No. 4,381,344) were added and the suspension stirred at 37° C. On day 6, the reaction was diluted to 250 ml with 5 mM potassium phosphate buffer, pH 7.0, which contained 0.04% (w/v) potassium azide and 0.49 g of 2-amino-6-methylaminopurine and 4,000 I.U. thymidine phosphorylase and 14,000 I.U. purine nucleoside phosphorylase were added. On day 14, the reaction was evaporated. The residue was suspended in methanol/water and the suspension filtered. The filtrate was evaporated. The residue was dissolved in water and applied to a 2.5×13 cm column of anion exchange resin (Bio-Rad AG1X2-hydroxide form). After washing the column with water, the product was eluted with methanol/water (1/1). After the solvent was removed under vacuum, the residue was dissolved in water and filtered through a 0.22 μm-pore membrane filter. Lyophilization of the filtrate yielded title compound that anlyzed as a 0.5 hydrate.

mp. 172° C. UV λmax nm (ε×$10^{-3}$): 0.1N HCl, 292.5 (11.5), 255 (12.1); pH 7, 279.5 (13.4), 263 (sh); 0.1N NaOH, 280 (13.7), 263 (sh).

Anal. Calcd. for $C_{11}H_{15}FN_6O_3$ 0.5 $H_2O$: Calcd.: C, 43.00; H, 5.25; N, 27.35; F, 6.18. Found: C, 42.99; H, 5.28; N, 27.33; F, 6.16.

$^1$H-NMR (200 mHz, $Me_2SO$-d6): δ 7.92 (s, 1H, H-8); 7.28 (bs, 1H, 6-NH); 6.13 (dd, 1H, H-1′, JF,1′=16.3 Hz, J=3.3 Hz); 5.91 (bs, 2H, 2-NH2); 5.64 (d, 1H, 3′-OH, J=5.8 Hz); 5.29 (ddd, 1H, H-2′, JF,2′=53.0 Hz, J1′,2′=3.3 Hz, J2′,3′=4.4 Hz); 5.27 (t, 1H, 5′-OH, J=5.5 Hz); 4.37 (m, 1H, H-3′); 3.92 (m, 1H, H-4′); 3.72 (m, 1H, H$_\alpha$-5′); 3.60 (m, 1H, H$_\beta$-5′); 2.86 (bs, 3H, N-CH3).

EXAMPLE 17

9-(2-Deoxy-2-fluoro-β-D-ribofuranosyl)hypoxanthine

6-Amino-9-(2-deoxy-2-fluoro-β-D-ribofuranosyl)-9H-purine (0.29 g, 1.0 mmole), prepared as in Example 8, was dissolved in 100 ml of water. Calf intestinal adenosine deaminase (4 I.U., Boehringer Mannheim) was added and the solution incubated at 37° C. for 24 hrs. The solvent was removed under vacuum. The residue was dissolved in water/n-propanol (7/3) and chromatographed on a 5×90 cm column of Sephadex G-10 (Pharmacia LKB) with water/n-propanol (7/3) as the solvent. Product-containing fractions were combined and the solvent removed under vacuum. The residue was dissolved in water and lyophilized to obtain title compound that analyzed as a hydrate.

mp. 175° C. (partial melt at 125°) UV λmax nm (ε×$10^{-3}$): 0.1N HCl, 249 (11.8); pH 7, 248.5 (12.0); 0.1N NaOH, 253 (13.0).

Anal. Calcd. for $C_{10}H_{11}FN_4O_4H_2O$: Calcd.: C, 41.67; H, 4.55; N, 19.44; F, 6.59. Found: C, 41.72; H, 4.58; N, 19.46; F, 6.37.

$^1$H-NMR (300 mHz, $Me_2SO$-d6): δ 8.33 and 8.09 (2s, 2H, H-8 and H-2); 6.21 (dd, 1H, H-1′, JF,1′=16.8 Hz, J=2.4 Hz); 5.75 (bs, 1H, 3′-OH), 5.36 (ddd, 1H, H-2′, JF,2′=52.7 Hz, J1′,2′=2.4 Hz, J1′,3′=4.4 Hz); 5.20 (bs, 1H, 5′-OH); 4.43 (apparent d m, 1H, H-3′, JF,3′=18.9 Hz); 3.97 (m, 1H, H-4′); 3.75 (m, 1H, H$_\alpha$-5′); 3.59 (m, 1H, H$_\beta$-5′)

EXAMPLE 18

2-Amino-9-(2-deoxy-2-fluoro-β-D-ribofuranosyl)-6-propoxy-9H-purine

2-Amino-6-propoxypurine (0.3 g, 1.6 mmoles) which may be prepared according to R. W. Balsiger and J. A. Montgomery (J. Org. Chem. 25:1573, 1960) and 1-(2-deoxy-2-fluoro-β-D-ribofuranosyl)uracil (0.52 g, 2.1 mmoles) which may be prepared according to J. F. Codington et al. (J. Org. Chem. 29:558, 1964) were suspended in 50 ml of 2 mM potassium phosphate buffer, pH 7.0, which contained 0.04% (w/v) potassium azide. The pH of the suspension was adjusted to 7.0 with KOH. Thymidine phosphorylase (4,000 I.U.) and purine nucleoside phosphorylase (14,000 I.U.) (T. A. Krenitsky et al., Biochemistry 20:3615, 1981 and U.S. Pat. No. 4,381,344) were added and the reaction stirred at 37° C. On day 6, the reaction was diluted to 250 ml with 5 mM potassium phosphate buffer, pH 7.0, which contained 0.04% (w/v) potassium azide, and 4,000 I.U. of thymidine phosphorylase and 14,000 I.U. of purine nucleoside phosphorylase were added. On day 14, the solvent was removed under vacuum. The residue was suspended in methanol/water and the suspension was filtered. The filtrate was evaporated. The residue was dissolved in hot water and applied to a 2.5×13 cm column of anion exchange resin (Bio-Rad AG1X2 hydroxide form). After washing the column with water, the product was eluted with methanol/water (1/1). Product-containing fractions were combined and the solvent removed under vacuum. The residue was dissolved in water and lyophilized to obtain title compound that analyzed as 0.9 hydrate.

mp. 93° C. (partial melt at 65° C.) UV λmax nm (ε×$10^{-3}$): 0.1N HCl, 289 (9.05), 245 (7.37); pH 7, 280 (9.28), 248 (9.82); 0.1N NaOH, 280.5 (9.67), 249.5 (9.55).

Anal. Calcd. for $C_{13}H_{18}FN_5O_4$ 0.9 $H_2O$: Calcd.: C, 45.69; H, 5.78; N, 20.49; F, 5.56. Found: C, 45.75; H, 5.61; N, 20.51; F, 5.60.

$^1$H-NMR (200 mHz, $Me_2SO$-d6): δ 8.09 (s, 1H, H-8); 6.49 (bs, 2H, 2-NH2); 6.08 (dd, 1H, H-1, JF,1′=16.4 Hz, J=2.7 Hz); 5.65 (d, 1H, 3′-OH, J=6.0 Hz); 5.42 (apparent t, 0.5H, 0.5 (H-2′), J=3.5 Hz); 5.14 (m, 1.5H, 0.5 (H-2′) and 5′-OH); 4.36 (m, 3H, H-3′; and 6-OCH2); 3.92 (m, 1H, H-4′); 3.69 (m, 1H, H$_\alpha$-5′); 3.60 (m, 1H, H$_\beta$-5′); 1.75 (apparent sextet, 2H, CH2, J=7.1 Hz); 0.95 (t, 3H, CH3, J=7.4 Hz).

EXAMPLE 19

2-Amino-9-(2-deoxy-2-fluoro-β-D-ribofuranosyl)-6-iodo-9H-purine

2-Amino-6-iodopurine (0.8 g, 3.1 mmoles) which may be prepared according to R. T. Koda et al. (J. Pharm. Sci. 57:2056, 1968) and 1-(2-deoxy-2-fluoro-β-D-ribofuranosyl)uracil (0.39 g, 1.6 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. The pH of the suspension was adjusted to 7.2 with KOH. Thymidine phosphorylase (2,000 I.U.) and purine nucleoside phosphorylase (3,250 I.U.) (T. A. Krenitsky et al., Biochemistry 20:3615, 1981 and U.S. Pat. No. 4,381,344) were added and the suspension stirred at 37° C. On day 12, the pH of the reaction was adjusted to 6.8 with acetic acid, and 2,000 I.U. of thymidine phosphorylase and 3,250 I.U. of purine nucleoside phosphorylase were added. On day 26, the reaction was diluted to 500 ml with 5 mM potassium phosphate buffer, pH 7, which contained 0.04% (w/v) potassium azide, and 2,000 I.U. thymidine phosphorylase and 3,250 I.U. purine nucleoside phosphorylase were added. On day 40, the reaction was filtered. The filtrate was evaporated. The residue was suspended in water/n-propanol (7/3) and filtered. The filtrate was evaporated. The residue was suspended in methanol and then filtered. The product which was contained in the filtrate was purified by chromatography on a 5×90 cm column of Biogel P-2 (Bio-Rad) with water/n-propanol (7/3) as the solvent, followed by chromatography on a 5×90 cm column of Sephadex G-10 (Pharmacia LKB) whith water/n-propanol (7/3) as the solvent. After the solvent was removed under vacuum, the residue was suspended in water and lyophilized to obtain title compound that analyzed as a 0.6 hydrate.

mp. 135° C. (partial melt at 108°–110° C.) UV λmax nm ($\epsilon \times 10^{-3}$): 0.1N HCl, 318 (7.94); pH 7, 315 (8.30); 0.1N NaOH, 315 (8.36).

Anal. Calcd. for $C_{10}H_{11}FIN_5O_3$ 0.6 $H_2O$: Calcd.: C, 29.59; H, 3.03; N, 17.25; F, 4.68; I, 31.26. Found: C, 29.69; H, 3.06; N, 17.22; F, 4.44; I, 31.47.

$^1$H-NMR (300 mHz, Me$_2$SO-d6): δ 8.33 (s, 1H, H-8); 6.96 (bs, 2H, 2-NH2); 6.09 (dd, 1H, H-1', JF,1'=16.7 Hz, J=2.4 Hz); 5.69 (d, 1H, 3'-OH, J=6.3 Hz); 5.33 (ddd, 1H, H-2', JF,2' 52.8 Hz, J1',2'=2.4 Hz, J2',3'=4.2 Hz); 5.16 (t, 1H, 5'-OH, J=5.3 Hz); 4.42 (m, 1H, H-3'); 3.95 (m, 1H, H-4'); 3.77 (m, 1H, H$\alpha$-5'); 3.60 (m, 1H, H$\beta$-5').

EXAMPLE 20

9-(2-Deoxy-2-fluoro-β-D-ribofuranosyl)-6-methylamino-9H-purine

6-Methylaminopurine (Sigma Chemical Company, 0.8 g, 5.4 mmoles) and 1-(2-deoxy-2-fluoro-β-D-ribofuranosyl)uracil (0.39 g, 1.6 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. Thymidine phosphorylase (2,400 I.U.) and purine nucleoside phosphorylase (3,900 I.U.) (T. A. Krenitsky et al., Biochemistry 20:3615, 1981 and U.S. Pat. No. 4,381,344) were added and the suspension stirred at 37° C. On day 6, the reaction was diluted to 100 ml with 5 mM potassium phosphate buffer, pH 7.0, which contained 0.04% (w/v) potassium azide. On day 17, the reaction was filtered. The filtrate was evaporated. The residue was suspended in methanol and then filtered. The filtrate was evaporated. The residue was dissolved in water and applied to a 2.5×7 cm column of anion exchange resin (Bio-Rad AG1X2-hydroxide form). The product was eluted with water. Product-containing fractions were combined and the solvent removed under vacuum. The residue was dissolved in water and filtered through a 0.2 μm-pore membrane filter. Lyophilization of the filtrate yielded title compound.

mp. 140° C. (shrinks at 65°, partial melt at 110° C.) UV λmax nm ($\epsilon \times 10^{-3}$): 0.1N HCl, 261.5 ((16.2); pH 7, 265.5 (15.0); 0.1N NaOH, 266 (15.3).

Anal. Calcd. for $C_{11}H_{14}FN_5O_3$: Calcd.: C, 46.64; H, 4.98; N, 24.72; F, 6.71. Found: C, 46.48; H, 5.07; N, 24.63; F, 6.93.

$^1$H-NMR (300 mHz, Me$_2$SO-d6): δ 8.37 and 8.25 (2s, 2H, H-8 and H-2); 7.86 (bs, 1H, 6-NH); 6.24 (dd, 1H, H-1', JF,1'=16.8 Hz, J=3.2 Hz); 5.74 (d, 1H, 3'-OH, J=6.1 Hz); 5.44 (ddd, 1H, H-2', JF,2'=53.0 Hz, J1',2'=3.2 Hz, J2',3'=4.4 Hz); 5.28 (t, 1H, 5'-OH, J=5.6 Hz); 4.49 (m, 1H, H-3'); 3.99 (m, 1H, H-4'); 3.75 (m, 1H, H$\alpha$-5'); 3.58 (m, 1H, H$\beta$-5'); 2.95 (bs, 3H, N-CH3).

EXAMPLE 21

9-(2-Deoxy-2-fluoro-β-D-ribofuranosyl)-6-ethoxy-9H-purine

6-Ethoxypurine (Sigma Chemical Company; 0.2 g, 1.2 mmoles) and 1-(2-deoxy-2-fluoro-β-D-ribofuranosyl)uracil (0.4 g, 1.6 mmoles) which may be prepared according to J. F. Codington et al. (J. Org. Chem. 29:558, 1964) were suspended in 20 ml of 5 mM potassium phosphate buffer, pH 7.0, which contained 0.04% (w/v) potassium azide. The pH of the suspension was adjusted to 7.0 with KOH and thymidine phosphorylase (2,000 I.U.) and purine nucleoside phosphorylase (5,540 I.U.) (T. A. Krenitsky et al., Biochemistry 20:3615, 1981 and U.S. Pat. No. 4,381,344 were added and the suspension stirred at 37° C. On day 5, and additional 2,000 I.U. thymidine phosphorylase and 2,770 I.U. of purine nucleoside phosphorylase were added. On day 9, 0.2 g 6-ethoxypurine was added. The pH of the reaction was adjusted to 7.0 with KOH and 2,000 I.U. thymidine phosphorylase and 5,540 I.U. purine nucleoside phosphorylase were added. On day 28, the suspension was filtered. The filtrate was applied to a 2.5×8.5 cm column of anion exchange resin (Bio-Rad AG1X2-hydroxide form). After washing with water, the product was eluted with methanol/water (3/7). Product containing fractions were combined and the solvent removed under vacuum. The product contained in the residue was further purified by chromatography on a 2.5×90 cm column of Biogel P-2 (Bio-Rad) with water/methanol (8/2) as the solvent followed by chromatography on a 2.5×50 cm silica gel column with acetonitrile/water (49/1) as the solvent. Product containing fractions were combined and the solvent removed under vacuum. The residue was dissolved in water and lyophilized to obtain title compound which analyzed as a 0.5 hydrate.

mp. 85°–87° C. (partial melt at 60°) UV λmax nm ($\epsilon \times 10^{-3}$): 0.1N HCl, 249 (11.4); pH 7, 248 (11.7); 0.1N NaOH, 249 (12.0).

Anal. Calcd. for $C_{12}H_{15}FN_4O_4$ 0.5 $H_2O$: Calcd.: C, 46.91; H, 5.25; N, 18.23; F, 6.18. Found: C, 46.80; H, 5.23; N, 18.21; F, 6.65.

$^1$H-NMR (200 mHz, Me$_2$SO-d6): δ 8.59 and 8.53 (2s, 2H, H-8 and H-2); 6.31 (dd, 1H, H-1', JF,1'=17.0 Hz, J=2.5 Hz); 5.70 (d, 1H, 3'-OH, J=6.3 Hz); 5.43 (ddd, 1H, H-2', JF,1'=52.9 Hz, J1',2'=2.5 Hz, J2',3'=4.4 Hz); 5.12 (t, 1H, 5'-OH, J=5.4 Hz); 4.59 (q, 2H, 6-OCH2, J=7.0 Hz); 4.51 (m, 1H, H-3'); 3.98 (m, 1H, H-4'); 3.73 (m, 1H, H$\alpha$-4'); 3.61 (m, 1H, H$\beta$-5'); 1.40 (t, 3H, -CH3, J=7.0 Hz).

EXAMPLE 22

2-Amino-9-(2-deoxy-2-fluoro-β-D-ribofuranosyl)-6-methylthio-9H-purine

2-Amino-6-methylthiopurine (Sigma Chemical Company; 0.6 g, 3.3 mmoles) and 1-(2-deoxy-2-fluoro-β-D-ribofuranosyl)uracil (0.3 g, 1.2 mmoles) which may be prepared according to J. F. Codington et al. (J. Org. Chem. 29:558, 1964) were suspended in 200 ml of 5 mM potassium phosphate buffer, pH 7.0, which contained 0.04% (w/v) potassium azide. Thymidine phosphorylase (4,000 I.U.) and purine nucleoside phosphorylase (6,500 I.U.) (T. A. Krenitsky et al., Biochemistry 20:3615, 1981 and U.S. Pat. No. 4,381,344) were added and the suspension stirred at 37° C. On day 14, the reaction was diluted to 400 ml with 5 mM potassium phosphate buffer, pH 7.0, which contained 0.04% (w/v) potassium azide and 8,000 I.U. thymidine phosphorylase and 6,500 I.U. purine nucleoside phosphorylase were added. On day 25, the pH of the reaction was adjusted to 6.9 with KOH. On day 39, the reaction was filtered. The filtrate was applied to a 2.5×13 cm column of anion exchange resin (Bio-Rad AG1X2-hydroxide form) and the product was eluted with methanol/water (3/7). After the solvent was removed under vacuum, the residue was suspended in water and lyophilized to obtain title compound that analyzed as a 0.5 hydrate.

mp. 85°–87° C. UV λmax nm ($\epsilon \times 10^{-3}$): 0.1N HCl, 327 (11.6), 250 (11.2), 263 (sh); pH 7, 311 (12.8), 257 (sh), 246 (15.1); 0.1N NaOH, 311 (13.3), 257 (sh), 246 (14.8).

Anal. Calcd. for $C_{11}H_{14}FN_5O_3S$ 0.5 $H_2O$: Calcd.: C, 40.74; H, 4.66; N, 21.59; F, 5.80, S, 9.89. Found: C, 40.79; H, 4.66; N, 21.55; F, 5.89, S, 9.84.

$^1$H-NMR (80 mHz, Me$_2$SO-d6): δ 8.17 (s, 1H, H-8); 6.57 (bs, 2H, 2-NH2); 6.14 (dd, 1H, H-1′, JF,1′=16.4 Hz, J=3.2 Hz); 5.64 (m 1.5H, 0.5 (H-2′) and 3′-OH); 5.11 (m, 1.5H, 0.5 (H-2′) and 5′OH); 4.40 (m 1H, H-3′); 3.95 (m, 1H, H-4′); 3.65 (m, 1H, H$_\alpha$-5′ and H$_\beta$-5′); 2.58 (s, 3H, 6-SCH3).

EXAMPLE 23

9-(2-Deoxy-2-fluoro-β-D-ribofuranosyl)-6-iodo-9H-purine

6-Iodopurine (Sigma Chemical Company; 0.7 g, 2.7 mmoles) and 1-(2-deoxy-2-fluoro-β-D-ribofuranosyl)uracil (0.4 g, 1.7 mmoles) which may be prepared according to J. F. Codington et al. (J. Org. Chem. 29:558, 1964) were suspended in 20 ml of 10 mM potassium phosphate buffer, pH 7.0, which contained 0.04% (w/v) potassium azide. Thymidine phosphorylase (2,640 I.U.) and purine nucleoside phosphorylase (4,360 I.U.) (T. A. Krenitsky et al., Biochemistry 20:3615, 1981 and U.S. Pat. No. 4,381,344) were added and the suspension stirred at 37° C. On day 21, the reaction was diluted to 50 ml with 5 mm potassium phosphate buffer, pH 7, which contained 0.04% (w/v) potassium azide and 4000 I.U. of thymidine phosphorylase and 6,500 I.U. of purine nucleoside phosphorylase were added. On day 43, the reaction was diluted to 250 ml with water and 2,000 I.U. thymidine phosphorylase and 3,250 I.U. purine nucleoside phosphorylase were added. On day 57, the reaction was filtered. The filtrate was evaporated. The residue was suspended in warm methanol and filtered. The filtrate was evaporated. The residue was dissolved in water/n-propanol (7/3) and applied to a 7.5×90 cm column of Biogel P-2 (Bio-Rad) with water/n-propanol (7/3) as the solvent. Product containing fractions were combined and the solvent removed under vacuum. The residue was dissolved in hot methanol and water added until a precipitate formed. The methanol was removed under vacuum. After standing overnight the suspension was filtered. The filter cake contained the bulk of the product. The filtrate was evaporated and the above procedure repeated to precipitate the remaining product. The filter cakes were combined and suspended in water. Lyophilization yielded the title compound.

mp. 198°–200° C. (dec.)

UV λmax nm ($\epsilon \times 10^{-3}$): 0.1N HCl, 275 (11.1), 257 (sh); pH 7, 275 (11.1), 258 (sh); 0.1N NaOH, 276 (9.98), 257 (sh), 303 (sh).

Anal. Calcd. for $C_{10}H_{10}$ FIN$_4$O$_3$ Calcd.: C, 31.60; H, 2.65; N, 14.74; F, 5.00; I, 33.39. Found: C, 31.70; H, 2.70; N, 14.69; F, 4.96; I, 33.48.

$^1$H-NMR (80 mHz, Me$_2$SO-d6): δ 8.87 and 8.66 (2s, 2H, H-8 and H-2); 6.35 (dd, 1H, H-1′, JF,1′=17.0 Hz, J=2.0 Hz); 5.76 (m, 1.5H, 0.5 (H-2′) and 3′-OH); 5.14 (m, 1.5H, 0.5 (H-2′) and 5′-OH); 4.51 (m, 1H, H-3′); 3.99 (m, 1H, H-4′); 3.70 (m, 2H, H$_\alpha$-5′ and H$_\beta$-5′).

EXAMPLE 24

Preparation of 9-(2-Deoxy-2-fluoro-5O-L-valinyl-β-D-ribofuranosyl)adenine and its bis-hydrochloride salt To a solution of 9-(2-deoxy-2-fluoro-β-D-ribofuranosyl)adenine (500 mg, 1.86 mmol), FMOC-L-valine (820 mg 1.3 eq) and DMAP (10 mg) in dry DMF (14 ml) at 0° C. was added a solution of DCC (Dicyclohexylcarbodiimide) (520 mg, 1.35 eq) in CH$_2$Cl$_2$ (2 ml) with stirring. The mixture was allowed to attain room temperature, stirred for 90 minutes and then evaporated in vacuo. After co-evaporation with ethanol the residue was taken up in CHCl$_3$/MeOH (9:1) and filtered. The filtrate was then evaporated and chromatographed over SiO$_2$ using the flash technique, eluting with a gradient of EtOH in CHCl$_3$ (5%–10%).

The first eluted fraction was the 3′,5′-bis ester (230 mg) containing some dicyclohexylurea. The second fraction was the 3′-mono ester and the third fraction was the 5′-mono ester (190 mg).

The 5′-FMOC protected valinate ester was then treated with a solution of piperidine (1 ml) in DMF (4 ml) at room temperature for 5 minutes, evaporated in vacuo, dissolved in water (25 ml) and washed with CHCl$_3$ (30 ml). The water was evaporated to produce a colourless gum, which was taken up in aqueous acetic acid, evaporated, and co-evaporated with ethanol and ether to provide the 5′-O-valinate ester as a hygroscopic amorphous solid (100 mg).

Anal. $C_{15}H_{21}FN_6O_4$. 1.5 $CH_3CO_2H$. 1.5 $H_2O$ requires: C 44.53; H 6.23; N 17.32 Found: C 44.38; H 6.32; N 16.94 mp. Decomposes above 150° C.

The bis-hydrochloride salt was prepared by dissolving 5′-O-valinate ester in isopropanol followed by the addition of isopropanol previously saturated with hydrogen chloride gas, and evaporation of the solvent. The white solid was then taken up in MeOH and precipitated with ether at 0° C. Filtration provided the bis-hydrochloride salt.

Anal. $C_{15}H_{21}FN_6O_4$. 2HCl. 0.5 $H_2O$ requires: C 40.00; H 5.37; N 18.67 Found: C 40.26; H 5.19; N 18.74 mp. 210°–213° (dec.)

EXAMPLE 25

2-Amino-9-(2-deoxy-2-fluoro-β-D-ribofuranosyl)-9H-purine bis hydrochloride

To a solution of 2-amino-9-(2-deoxy-2-fluoro-β-D-ribofuranosyl)-9H-purine (300 mg 1.11 mmol) in MeOH (20 ml) was added isopropanol (2.5 ml) previously saturated with hydrochloride (HCL) gas. Acetone (15 ml) was added and the solution evaporated to almost dryness under vacuum at room temperature. Trituration with ethyl acetate (15 ml) produced a white solid which was filtered and washed with ether.

mp. 160°–163° (dec)

Anal. $C_{10}H_{12}F$ $N_5O_3$.2 HCL requires: C, 35.01; H, 4.12; N, 20.42; F, 5.55 Found: C, 34.79; H, 4.23; N, 20.32; F, 5.66

EXAMPLE 26

2,6-Diamino-9-(2-deoxy-2-fluoro-β-D-ribofuranosyl)-9H-purine bis hydrochloride To a solution of 2,6-diamino-9-(2-deoxy-2-fluoro-β-D-ribofuranosyl)-9H-purine (300 mg, 1.06 mmol) in MeOH (30 ml) was added ispropanol (2 ml) previously saturated with HCl gas. The solution was evaporated to a small volume (5 ml) at room temperature, and EtOH (15 ml) added to precipitate the bis hydrochloride as a white solid.

mp. 165°–168° C. (dec)

Anal. $C_{10}H_{13}FN_6O_3 \cdot 2$ HCl requires: C, 33.62; H, 4.23; H, 23.53; F, 5.32 Found: C, 33.54; H, 4.24; N, 22.98; F, 5.33

EXAMPLE 27

Sodium Salt of 9-(2-deoxy-2-fluoro-β-D-ribofuranosyl)guanine

To 9-(2-deoxy-2-fluoro-β-D-ribofuranosyl)guanine (50 mg, 0.175 mmol) was added a solution of NaOH (7 mg) in water (2 ml) and the mixture warmed gently until a clear solution was obtained. The solution was then lyophilised to afford the title compound as a white solid.

mp. 185°–190° C. (dec)

Anal. $C_{10}H_{11}FN_5O_4$ N, 1.75 $H_2O$ requires: C, 35.45; H, 4.31; N, 20.67 Found: C, 35.59; H, 4.33; N, 20.64

EXAMPLE 28

9-(2-Deoxy-2-fluoro-β-D-ribofuranosyl)guanine hydrochloride

To a solution of 9-(2-deoxy-2-fluoro-β-D-ribofuranosyl)guanine (300 mg. 1.05 mmol) in MeOH (200 ml) was added a solution of isopropanol, (2 ml) previously saturated with HCl gas, followed by acetone (50 ml). The solution was evaporated to a small volume (30 ml), acetone (150 ml) added, and the mixture again reduced to a small volume. This was repeated, the final volume being 10 ml. EtOH (20 ml) was added, followed by EtOAc (40 ml). On standing, the product precipitated as a white solid.

mp. 192°–193° C. (dec)

Anal. $C_{10}H_{12}FN_5O_4$ HCl 0.4 $H_2O$ requires: C, 36.51; H, 4.23; N, 21.29; N, 10.77 Found: C, 36.50; H, 4.54, N, 21.36, N, 10.90

EXAMPLE 29

9-(2-Deoxy-2-fluoro-β-D-ribofuranosyl)adenine hydrochloride

To a solution of 9-(2-deoxy-2-fluoro-β-D-ribofuranosyl)adenine (500 mg. 1.86 mmol) in MeOH (40 ml) and water (10 ml) was added a solution of isopropanol (15 ml) previously saturated with HCl gas. The solution was evaporated under vacuum at room temperature, and triturated with EtOH (25 ml) to afford the title compound as a white solid.

mp. 205°–210° (dec)

Anal. $C_{10}H_{12}FN_5O_3$ HCl requires: C, 39.29; H, 4.29; N, 22.91; CL, 11.60 Found: C, 39.36; H, 4.34; N, 22.89; CL, 11.52

EXAMPLE 30

9-(2-Deoxy-2-fluoro-β-D-ribofuranosyl)adenine-5'-monophosphate 9-(2-deoxy-2-fluoro-β-D-ribofuranosyl)adenine (of Example 8, 0.47 g, 1.7 mmol) was dissolved in 7 ml of 1,3-dimethyl-3,4,5,6-tetrahydro-2(1H)-pyrimidinone. After cooling this solution to −8° C. in an ice/methanol bath, 0.64 ml phosphorus oxychloride (7 mmol) was added with vigorous stirring. After three minutes the reaction was stopped by adding 10 ml cold water. This reaction mixture was kept on ice for 15 min, then neutralized to pH 8 with ammonium hydroxide.

Separation of the reaction products was performed using anion exchange chromotography on DEAE Sephadex A-25. The reaction mixture was diluted to 600 ml with water and applied to a chromatography column containing about 80 ml of DEAE Sephadex A-25 which had been previously equilibrated in 50 mM ammonium bicarbonate. The column was washed with 2.5 L of 50 mM ammonium bicarbonate to remove inorganic phosphate. The nucleotides were eluted with a 2 L linear gradient of 50–500 mM ammonium bicarbonate. 9-(2-deoxy-2-fluoro-β-D-ribofuranosyl)adenine-5'-monophosphate eluted first followed by 9-(2-deoxy-2-fluoro-β-D-ribofuranosyl)adenine-3',5'-bisphosphate. Fractions containing each nucleotide were pooled and dried in vacuo to remove water and ammonium bicarbonate.

9-(2-deoxy-2-fluoro-β-D-ribofuranosyl)adenine-5'-monophosphate was obtained as the ammonium salt from the above scheme but the sodium salt was the pharmacologically desired salt in this case. The ammonium salt was exchanged for sodium using Dowex 50 ion exchange resin. 9-(2-deoxy-2-fluoro-β-D-ribofuranosyl)adenine-5'-monophosphate (1.3 mmol) in 10 ml water was applied to a column containing about 10 ml of BioRad AG50W-X8 (sodium form) which had been previously equilibrated with water. The nucleotide was eluted with water. Fractions containing 9-(2-deoxy-2-fluoro-β-D-ribofuranosyl)adenine-5'-monophosphate combined and lyophilized to give 0.49 g (1.2 mmol, 72% yield).

$^1$H-NMR d ($d_6$-DMSO) δ 8.0 (1H, s, H2), 7.7 (1H, s, H8), 5.7 and 5.9 (1H, dd, H1', split by H2',F), 4.8 and 5.0 (1H dd, H2', split by H1',F), 4.1 (1H, m, H3'), 3.9 (1H, m, H4'), 3.6 (2H, m, H5')

$^1$H-NMR d ($D_2O$) 8.5 (1H, s, H2), 8.2 (1H, s, H8), 6.3 and 6.5 (1H, d, H1', split by H2',F), 5.3 and 5.6 (1H, d, H2', split by H1',F), 4.7 (1H, m, H3'), 4.4 (1H, m, H4'), 4.1 (2H, m, H5') 31P NMR δ ($D_2O$) 1.46 (s)

UV spectra: in 0.1M HCl λmax at 256 nm; in 400 mM ammonium phosphate, pH 5.5 λmax at 259 nm; in 50 mM potassium phosphate, pH 7.0 max at 259 nm; in 0.1M NaOH λmax at 259 nm.

Mass spectrum gave two main peaks at molecular ion fragment weights of 270 and 136, corresponding to 9-(2-deoxy-2-fluoro-β-D-ribofuranosyl)adenine, respectively.

Total cleavage to the nucleoside was observed after incubation with 5'-nucleotidase (Sigma).

Base/phosphate ratio=1.00/1.03. The concentration of total phosphate was determined by the method of Ames, B. N. in Methods in Enzymology Vol. 8 pp. 115–118, 1966. The concentration of nucleobase was determined using the UV extinction coefficient of the nucleoside.

EXAMPLE 31

9-(2-Deoxy-2-fluoro-β-D-ribofuranosyl)adenine-5'-monophosphate (FMAP)

9-(2-Deoxy-2-fluoro-β-D-ribofuranosyl)adenine (of Example 8, 1.2 mg, 4.3 µmol), 22 µmol p-nitrophenylphosphate (1M stock adjusted to pH 5.4 with acetic acid) and 0.05 ml of nucleoside phosphotransferase from *Serratia marcescens* [A. Fyfe, et al., J. Biol. Chem. 253, 8721–8727 (1978) and U.S. Pat. No. 4,136,175 Jan. 23, 1979] were combined with water to give a final volume of 0.22 ml. Incubation was done at 37° C. overnight. The entire reaction was spotted onto a preparative cellulose thin layer chromatography plate then developed in n-propanol/15M NH$_4$OH/H$_2$O: 6/3/1. After drying the plate, the area containing nucleotide was scraped off and the nucleotide was eluted from the cellulose with water. 9-(2-Deoxy-2-fluoro-β-D-ribofuranosyl)adenine-5'-monophosphate was obtained in 25% yield, 1.1 µmol.

UV spectra: in water, λmax at 257 nm.

This compound was completely cleaved by alkaline phosphatase and 5'-nucleotidase to give the nucleoside 9-(2-deoxy-2-fluoro-β-D-ribofuranosyl)adenine.

Base/phosphate ratio=1/8, indicating contamination by inorganic phosphate.

EXAMPLE 32

9-(2-Deoxy-2-fluoro-β-D-ribofuranosyl)adenine-3',5'-bisphosphate

The 9-(2-Deoxy-2-fluoro-β-D-ribofuranosyl)adenine-3',5'-bisphosphate was obtained as the ammonium salt after evaporation of fractions from the ion-exchange column {of example 30} (0.35 mmol, 20% yield).

This was characterised by the pattern of spots observed on TLC after incubation with nuclease P1 (Boehringer Mannheim), alkaline phosphatase (Boehringer Mannheim), 3-nucleotidase (Sigma) and 5'-nucleotidase. Alkaline phosphatase totally cleaved 9-(2-Deoxy-2-fluoro-β-D-ribofuranosyl)adenine-3',3'-bisphosphate to the parent nucleoside; nuclease P1 and 3-nucleotidase cleaved it to 9-(2-Deoxy-2-fluoro-β-D-ribofuranosyl)adenine-5'-monophosphate and 5'-nucleotidase did not cleave it. These results were consistent with what is known for these enzymes and other known nucleoside phosphate analogs.

UV spectra: in 400 mM ammonium phosphate, pH 5.5 max at 259 nm.

EXAMPLE 33

9(2-Deoxy-2-fluoro-β-D-ribofuranosyl)guanine-5'-monophosphate 9-(2-Deoxy-2-fluoro-β-D-ribofuranosyl)guanine (of Example 7, 0.9 mg, 2.9 µmol), 15 µmol p-nitrophenylphosphate (1M stock adjusted to pH 5.4 with acetic acid) and 0.04 ml of nucleoside phosphotransferase from *Serratia marcescens* [Fyfe, et al., J. Biol. Chem. 253, 8721–8727 (1978) and U.S. Pat. No. 4,136,175 Jan. 23, 1979] were combined with water to give a final volume of 0.15 ml. Incubation was done at 37° C. overnight. The entire reaction was spotted onto a preparative cellulose thin layer chromatograph plate then developed in n-propanol/15M NH$_4$OH/H$_2$O: 6/3/1/ After drying the plate, the area containing nucleotide was scraped off then the nucleotide was eluted from the cellulose with water. 9-(2-Deoxy-2-fluoro-β-D-ribofuranosyl)guanine-5'-monophosphate was obtained in 11% yield, 0.33 µmol. UV spectra: in water, max at 248 nm, shoulder at 267 nm.

This compound was completely cleaved by alkaline phosphatase and 5'-nucleotidase to give nucleoside 9-(2-deoxy-2-fluoro-β-D-ribofuranosyl)guanine.

Base/phosphate ratio=1/30, indicating contamination by inorganic phosphate.

EXAMPLE 34

9-(2-Deoxy-2-fluoro-β-D-ribofuranosyl)guanine-5'-monophosphate (FGMP)

9-(2-Deoxy-2-fluoro-β-D-ribofuranosyl)guanine (0.0158 g; $5.2 \times 10^{-5}$ mol) was dissolved in 0.2 ml triethylphosphate and cooled to −8° C. Phosphorous oxychloride (0.015 ml; $1.6 \times 10^{-4}$ mol) was added all at once with stirring and the reaction vessel covered with aluminum foil to protect the reactants from light. The temperature was allowed to come to 0° C. and stirred for 4 hours. The reaction was quenched by addition of ice then the pH value adjusted to pH7 with 1N NaOH. this aqueous solution was extracted with CHCl$_3$ 2×2 ml. The pH value of the aqueous solution was readjusted to pH 7.5.

This compound was purified by DEAE Sephadex chromatography similarly to 2'-FAMP in example 30, but with a 50–600 mM ammonium bicarbonate gradient. The yield of diammonium salt was 40%, 9 mg, 0.02 mmol.

UV spectra: in 0.1M HCl λmax at 254 nm, shoulder at 275 nm.

This compound was completely cleaved by alkaline phosphatase and 5'-nucleotidase to give nucleoside 9-(2-deoxy-2-fluoro-β-D-ribofuranosyl)guanine.

Base/phosphate ratio=1.0/0.90.

EXAMPLE 35

9-(2-Deoxy-2-fluoro-β-D-ribofuranosyl)guanine-5'-triphosphate (FGTP)

The triphosphate was enzymatically synthesized from the 5'-monophosphate. Five mg (12 µmol) of 2'-FGMP of example 34 was incubated at 37° C. in a final volume of 2 ml with (final concentration): 10 mM adenosine triphosphate, 50 mM potassium PIPES, pH 6.8, 10 mM MgCl$_2$, 12.5 mM phosphoenolpyruvate, 4 IU/ml nucleoside diphosphate kinase (Boehringer Mannheim), 0.77 IU/ml guanylate kinase (Boehringer Mannheim) and 20 IU/ml pyruvate kinase (Boehringer Mannheim). Small amounts of 9-(2-Deoxy-2-fluoro-β-D-ribofuranosyl)guanine-5'-diphosphate (FGDP) were observed by analytical ion-exchange HPLC, but the predominant product was 9-(2-Deoxy-2-fluoro-β-D-ribofuranosyl)guanine-5'-triphosphate. This was isolated using preparative ion exchange HPLC on a Whatman Partisil SAX Magnum 9 column eluted with a gradient of 10 mM–1M potassium phosphate pH 3.5. The fractions containing 2'-FGTP were further purified on DEAE Sephadex as described in example 30. After drying the fractions, 7 mg of 2'-FGTP as the diammonium salt was obtained (80%, 10 µmol).

UV spectra: in 0.1M HCl λmax at 254 nm, shoulder at 275 nm; in 0.1M NaOH λmax at 255–262 nm.

Base/phosphate ratio=1.0/2.5.

EXAMPLE 36

9-(2-Deoxy-2-fluoro-β-D-ribofuranosyl)guanine-5'-triphosphate

Fifty mg (120 μmol) of 2'-FGMP, prepared in a manner analogous to example 34, was incubated at 37° C. in a final volume of 20 ml with (final concentration): 10 mM adenosine triphosphate, 50 mM potassium PIPES, pH 6.8, 10 mM MgCl$_2$, 12.5 mM phosphoenolpyruvate, 4 IU/ml nucleoside diphosphate kinase (Boehringer Mannheim), 0.77 IU/ml guanylate kinase (Boehringer Mannheim) and 20 IU/ml pyruvate kinase (Boehringer Mannheim). Small amounts of 9-(2-deoxy-2-fluoro-β-D-ribofuranosyl)guanine-5'-diphosphate were observed by analytical ion-exchange HPLC, but the predominant product was 9-(2-deoxy-2-fluoro-β-D-ribofuranosyl)-guanine-5'-triphosphate. This was isolated using preparative ion-exchange HPLC on a Whatman Partisil SAX Magnum 9 column eluted with a gradient of 10 mM-1M potassium phosphate pH 3.5. The fractions containing 2'-FGTP were further purified on DEAE Sephadex as described in example 30. After drying the fractions, 50 mg of 2'-FGTP as the diammonium salt was obtained but it was contaminated with adenosine diphosphate, 2'-FGDP and adenosine triphosphate. A repeat purification of preparative HPLC followed by DEAE Sephadex was done. The triammonium salt was obtained (36 mg, 63 μmol, 50% yield).

UV spectra: in 0.1M HCl λmax at 254 nm, should at 275 nm.

Base/phosphate ratio = 1.0/2.9.

EXAMPLE 37

2,6-Diamino-9-(2-deoxy-2-fluoro-3,5-di-O-pivaloyl-β-D-ribofuranosyl)-9H-purine and
2,6-diamino-9-(2-deoxy-2-fluoro-5-o-pivaloyl-β-D-ribofuranosyl)-9H-purine To a solution of 2,6-diamino-9-(2-deoxy-2-fluoro-β-D-ribofuranosyl)-9H-purine (100 mg, 0.35 mmol) in a solution of DMF (3 ml) and Et$_3$N (0.3 ml) was added trimethylacetic anhydride (78 μl) and the solution stirred at room temperature overnight. A further 80 μl of trimethylacetic anhydride was then added and stirring continued for 3 days. The mixture was then quenched with MeOH, evaporated in vacuo and chromatographed over flash SiO$_2$, eluting w/ CHCl$_3$, CHCl$_3$/MeOH (30:1), (20:1), (10:1), (6:1), (4:1) and finally (3:1). This gave the bis-ester (74 mg) as a colourless semi-solid after trituration with ether.

mp. 143°–145° C. (dec.)

High resolution mass spectrum (E.I.): Found: 368.1612 C$_{15}$ H$_{21}$ FN$_6$ O$_4$ requires 368.1608.

Collection and evaporation of the appropriate fractions also gave the mono-5'-pivalate ester (16 mg).

mp. 123°–125° C.

High resolution mass spectrum (E.I.): Found: 452.2181 C$_{20}$ H$_{29}$ FN$_6$ O$_5$ required 452.2183.

EXAMPLE 38

2-Amino-6-benzylamino-9-(2'-deoxy-2'-fluoro-β-D-ribofuranosyl)-9H-purine

2-Amino-6-benzylaminopurine (0.2 g, 0.83 mmole) and 1-(2-deoxy-2-fluoro-β-D-ribofuranosyl)uracil (0.244 g, 1 mmole) were combined with 10 ml of 10 mM potassium phosphate buffer, pH 6.8. 8200 units of thymidine phosphorylase and 7850 units of purine nucleoside phosphorylase (Krenitsky, et al *Biochemistry*, 20, 3615, 1981 and U.S. Pat. No. 4,381,444) were added and the mixture stirred at 45° C. for 40 hours. Product isolation was accomplished by adding methanol (15 ml), removal of the solids by filtration, and evaporating the methanol in the presence of 10 ml silica gel. The dry gel was applied to the top of a column of silica (5×23 cm) and the product eluted with chloroform:methanol (99:1). The fractions containing only the product were combined the solvent removed under vacuum resulting in 0.087 g of 2-amino-6-benzylamino-9-(2'-deoxy-2'-fluoro-β-D-ribofuranosyl)-9H-purine.

$^1$H-NMR (200 mHz): δ 7.95 (s, 1 H, H$_8$), 7.85 (b, 1H, NH), 7.2–7.5 (m, 5H, phenyl), 6.04 (dd, 1H, H$_{1'}$,$J$,$_{1'}$ = 16.4 Hz, J=3.1 Hz) 5.93 (b, 2H, NH$_2$), 5.64 (d, 1H, OH, J=5.9 Hz), 5.44, 5.17 (dt, 1H, H$_{2'}$), 5.26 (t, 1H, OH$_{5'}$), 4.64 (b, 2H, CH$_2$), 4.38 (m, 1H H$_{3'}$), 3.9 (b, 1H, H$_{4'}$), 3.5–3.75 (m, 2H, H$_{5'}$).

Reduction of the above compound may be accomplished according to the procedures of V.du Vigneaud and O. K. Behrens J. Biol. Chem. 117, 27 (1937).

EXAMPLE 39

2-Amino-6-benzylthio-9-(2-deoxy-2-fluoro-β-D-ribofuranosyl)-9H-purine

2-Amino-6-benxylthiopurine (Sigma Chemical Company; 0.8 g, 3.1 mmoles) and 1-(2-deoxy-2-fluoro-β-D-ribofuranosyl)uracil (0.4 g, 1.7 mmoles) which may be prepared according to J. F. Codington et al., (*J. Org. Chem.* 29:558, 1964) were suspended in 20 ml of 10 mM potassium phosphate buffer, pH 7.0, which contained 0.04% (w/v) potassium azide. Thymidine phosphorylase (2,640 I.U.) and purine nucleoside phosphorylase (4,360 I.U.) (T. A. Krenitsky et al., *Biochemistry* 20:3615, 1981 and U.S. Pat. No. 4,381,344) were added and the suspension stirred at 37° C. On day 21, the reaction was diluted to 150 ml with 5 mM potassium phosphate buffer, pH 7.0, which contained 0.04% (w/v) potassium azide and 4,000 I.U. thymidine phosphorylase and 6,500 I.U. purine nucleoside phosphorylase were added. On day 43, the reaction was diluted to 250 ml with water and 2,000 I.U. thymidine phosphorylase and 3,250 I.U. purine nucleoside phosphorylase were added. On day 69, the pH of the reaction was adjusted to 7.1 with KOH. On day 77, the reaction was evaporated. The residue was dissolved in hot methanol/water and applied to a 2.5×7 cm column of anion exchange resin (Bio-Rad AG1X2-hydroxide form) and the product was eluted with methanol/water (9/1). Product containing fractions were combined and the solvent removed under vacuum. The residue was dissolved in acetonitrile/water (49/1) and applied to a 2.5×20 cm column of silica gel 60 (EM Science). The product was eluted with acetonitrile/water (49/1). Product containing fractions were combined and the solvent removed under vacuum. The residue was suspended in water and lyophilization yielded 0.201 g of title compound that analyzed as a 0.1 hydrate.

mp. 180° C.

UV λmax nm ($\epsilon \times 10^{-3}$): 0.1N HCl, 322.5 (11.8), 250 (10.6); pH 7, 311.5 (14.2), 247 (14.3); 0.1N NaOH, 312 (14.0), 247 (13.5).

Anal. Calcd. for C$_{17}$H$_{18}$FN$_5$O$_3$S.0.1 H$_2$O: Calcd.: C, 51.93; H, 4.66; N, 17.81; F, 4.83, S, 8.15 Found: C, 51.96; H, 4.66; N, 17.86; F, 4.68, S, 8.15

$^1$H-NMR (300 mHz, Me$_2$SO-d$_6$): δ 8.19 (s, 1H, H-8), 7.47 (apparent d, 2H, Ar, J=7.6 Hz), 7.28 (m, 3H, Ar), 6.74 (bs, 2H, 2-NH$_2$), 6.10 (dd, 1H, H-1', $J$F, 1'=16.6

Hz, J=2.4 Hz), 5.68 (d, 1H, 3'-OH, J=6.4 Hz), 5.32 (ddd, 1H, H-2', $J_{F},2'=53.0$ Hz, $J_{1',2'}=2.4$ Hz, $J_{2',3'}=4.4$ Hz, 5.15 (t, 1H, 5'-OH, J=6.0 Hz, 4.55 (ab quartet, 2H, 6-SCH$_2$, geminal J=−13.7 Hz), 4.41 (m, 1H, H-3'), 3.94 (m, 1H, H-4'), 3.74 (m, 1H, H$_\alpha$-5'), 3.58 (m, 1H, H$_\beta$-5').

EXAMPLE 40

2,6-Diamino-9-(2-deoxy-2-fluoro-β-D-ribofuranosyl)-9H-purine 2,6-Diaminopurine (Pacific Chemical Laboratories, 2.0 g, 12.7 mmoles) and 1-(2-deoxy-2-fluoro-β-D-ribofuranosyl)uracil (0.8 g; 3.3 mmoles) which may be prepared according to J. F. Codington et al., (*J. Org. Chem.* 29:558, 1964) were suspended to 500 ml of 5 mM potassium phosphate buffer, pH 7.0, which contained 0.04% (w/v) potassium azide. Thymidine phosphorylase (41,700 I.U.) and purine nucleoside phosphorylase (83,300 I.U.) (T. A. Krenitsky et al., *Biochemistry* 20:3615, 1981 and U.S. Pat. No. 4,381,344) which had been absorbed onto 10.5 g of DEAE-cellulose (25 ml) were added and the suspension shaken at 37° C. After 24 hours 2.0 g of 1,6-diaminopurine was added and the temperature increased to 50° C. After another 24 hours the reaction was filtered. The filter cake was washed with water and the filtrates combined and the solvent removed under vacuum. The residue was dissolved in hot water and the pH adjusted to pH 9.4 with NH$_4$OH. The solution was applied to a 2.5×13 cm column of anion exchange resin (Bio-Rad AG1X2-hydroxide form). After washing the column with water, the product was eluted with methanol/water (9/1). Product containing fractions were combined and the solvent removed under vacuum. The residue was treated as above. Product containing fractions were combined and the solvent removed under vacuum. The residue was dissolved in water and lyophilization yielded 0.89 g of title compound that analyzed as a 0.5 hydrate.

mp. 125°–127° C.

UV λmax nm ($\epsilon \times 10^{-3}$): pH 7, 279.5 (9.52, 256 (9.06);

Anal. Calcd. for C$_{10}$H$_{13}$FN$_6$O$_3$—0.5 H$_2$O: Calcd: C, 40.96; H, 4.81; N, 28.66; F, 6.48 Found: C, 41.03; H, 4.80; N, 28.69; F, 6.50

Structure further confirmed by $^1$H-NMR.

EXAMPLE 41

2-Amino-9-(2-deoxy-2-fluoro-β-D-ribofuranosyl)-9H-purine

2-Aminopurine (Pacific Chemical Laboratories, 3.0 g, 22.2 mmoles) and 1-(2-deoxy-2-fluoro-β-D-ribofuranosyl)uracil (0.5 g; 2.0 mmoles) which may be prepared according to J. F. Codington et al., (*J. Org. Chem.* 29:558, 1964) were suspended in 25 ml of 5 mM potassium phosphate buffer, pH 7.0, which contained 0.04% (w/v) potassium azide. Thymidine phosphorylase (41,700 I.U.) and purine nucleoside phosphorylase (83,300 I.U.) (T. A. Krenitsky et al., *Biochemistry* 20:3615, 1981 and U.S. Pat. No. 4,381,344) which had been absorbed onto 10.5 g of DEAE-cellulose (25 ml) were added and the suspension shaken at 37° C. After 24 hours 3.0 g of 2,6-diaminopurine was added and the temperature increased to 50° C. After another 24 hours the reaction was filtered. The filter cake was washed with water and the filtrates combined and the solvent removed under vacuum. The residue was suspended in water and filtered. The filter cake was extracted with water (25° C.) until no product remained in the filter cake. The filtrates were combined, the pH was adjusted to pH 9.4 with NH$_4$OH, and the solution applied to a 2.5×20 cm column of anion exchange resin (Bio-Rad AG1X2-hydroxide form). After washing the column with water, the product was eluted with methanol/water (9/1). Product containing fractions were combined and the solvent removed under vacuum. The residue was dissolved in chloroform/methanol/water (75:25:4) and applied to a 5×25 cm column of silica gel 60. The product was eluted with chloroform/methanl/water (75:25:4). Product containing fractions were combined and the solvent removed under vacuum. The residue was dissolved in hot water and filtered through a 0.22 μm-pore membrane filter. Lyophilization of the filtrate yielded 0.50 g of title compound that analyzed as a 0.5 hydrate.

mp. 153°–155° C.

UV λmax nm ($\epsilon \times 10^{-3}$): pH 7, 304 (6.35), 243.5 (5.95)

Anal. Calcd. for C$_{10}$H$_{12}$FN$_5$O$_3$—0.5H$_2$O: Calcd.: C, 43.17, H, 4.71; N, 25.17; F, 6.83 Found: C, 43.08; H, 4.74; N, 25.11; F, 6.89

Structure further confirmed by $^1$H-NMR.

EXAMPLE 42

2-Amino-9-(2-deoxy-2-fluoro-β-D-ribofuranosyl)-6-methoxy-9H-purine

2-Amino-6-methoxypurine (2.0 g, 12 mmoles) which may be prepared according to R. W. Balsiger and J. A. Montgomery (*J. Org. Chem.* 20:1573, 1960) and 1-(2-deoxy-2-fluoro-β-D-ribofuranosyl)uracil (0.88 g; 3.6 mmoles) which may be prepared according to J. F. Codington et al., (*J. Org. Chem.* 29:558, 1964) were suspended in 250 ml of 5 mM potassium phosphate buffer, pH 7.0, which contained 0.04% (w/v) potassium azide. The pH of the suspension was adjusted to 7.0 with KOH. Thymidine phosphorylase (41,700 I.U.) and purine nucleoside phosphorylase (83.300 I.U.) (T. A. Krenitsky et al., *Biochemistry* 20:3615, 1981 and U.S. Pat. No. 4,381,344) which had been absorbed onto 10.5 g of DEAE-cellulose (25 ml) were added and the suspension shaken at 37° C. After 24 hours 1.0 g of 2-amino-6-methoxypurine and 250 ml of the above buffer were added and the temperature increased to 50° C. After another 24 hours the reaction was filtered. The filter cake was washed with water and the filtrates combined and the solvent removed under vacuum. The residue was dissolved in warm water and the pH adjusted to pH 9.4 with NH$_4$OH. The solution was applied to a 2.5×15 cm column of anion exchange resin (Bio-Rad AG1X2-hydroxide form). After washing the column with water, the product was eluted with methanol/water (9/1). Product containing fractions were combined and the solvent removed under vacuum. The residue was dissolved in warm water/methanol and filtered through a 0.22 μm-pore nylon membrane filter. Lyophilization of the filtrate yielded 0.91 g of title compound that analyzed as a 0.5 hydrate.

mp. 200° C.

UV λmax nm ($\epsilon \times 10^{-3}$): pH7; 279.5 (9.24), 247.5 (9.99).

Anal. Calcd. for C$_{11}$H$_{14}$FN$_5$O$_4$—0.5H$_2$O: Calcd.: C, 42.86; H, 4.90; N, 22.72; F, 6.16 Found: C, 42.93; H, 4.90; N, 22.73; F, 6.15

Structure further confirmed by $^1$H-NMR.

EXAMPLE 43

2-Amino-6-benzyloxy-9-(2-deoxy-2-fluoro-β-D-ribofuranosyl)-9H-purine

2-Amino-6-benxyloxypurine (2.5 g, 10.3 mmole) and 2'-deoxy-2'-fluoro-uridine (2.64 g, 10.8 mmole) were combined with 50 ml of 10 mM potassium phosphate buffer, pH 6.8. 8000 units of thymidine phosphorylase and 21600 units of purine nucleoside phosphorylase were added and the mixture stirred at 45° C. After five days an additional 16000 units of thymidine phosphorylase and 21600 units of purine nucleoside phosphorylase were added and the contents of the reaction stirred for 48 hours at 45° C. The majority of the product was contained in the precipitate which was removed by filtration and dissolved in methanol. Product was isolated by chromatography on silica with ethyl acetate:chloroform:methanol (8:1:1) as the mobile phase. Fractions containing only the product were combined and the solvent was evaporated to give 1.44 g of 2-amino-6-benxyloxy-9-(2 -deoxy-2-fluoro-β-D-ribofuranosyl)-9H-purine.

$^1$H-NMR (200 mHz in DMSO): δ 8.11 (s, 1H, H$_8$), 7.3–7.5 (m, 5H, phenyl), 6.59 (b, 2H, NH$_2$), 6.09 (dd, 1H, H$_{1'}$, J$_{F,1'}$=16.5 Hz, J=2.6 Hz), 5.66 (d, 1H, OH, J=6.1 Hz), 5.48 (s, 2H, CH$_2$), 5.25, 5.53 (bd, 1H, H$_{2'}$), 5.20 (m, 1H, OH$_{5'}$), 4.3–4.5) (m, 1H, H$_{3'}$), 3.9 (b, 1H, 4'), 3.5–3.8 (m, 2H, H$_{5'}$).

The generation of the compound of Example 7 from 2-amino-6-benzyloxy-9-(2-deoxy-2-fluoro-β-D-ribofuranosyl)-9H-purine is accomplished by the procedure of El Amin et al., J. Org. Chem., 44, 3442 (1979).

Pharmaceutical Formulations

In the following formulation Examples, the "Active Ingredient" may be any compound of formula (I) or a pharmaceutically acceptable salt thereof, for example compounds of Examples 6, 7, 9 and 12.

EXAMPLE 44 TABLET FORMULATIONS

The following formulations A, B and C are prepared by wet granulation of the ingredients with a solution of povidone, followed by addition of magnesium stearate and compression.

|  | mg/tablet | mg/tablet |
|---|---|---|
| Formulation A | | |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | | |
| Active ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients.

|  | mg/capsule |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation is prepared by wet granulation of the following ingredients with a solution of povidone followed by the addition of magnesium stearate and compression.

|  |  | mg/tablet |
|---|---|---|
| (a) | Active Ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

Drug release takes place over a period of about 6–8 hours and is complete after 12 hours.

EXAMPLE 45 CAPSULE FORMULATIONS

Formulation A

A capsule formulation is prepared by admixing the ingredients of Formulation D in Example 4 above and filling into a two-part hard gelatin capsule.

| Formulation B |  | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

Capsules are prepared by admixing the above ingredients and filling into a two-part hard gelatin capsule.

| Formulation C |  | mg/capsule |
|---|---|---|
| (a) | Active ingredient | 250 |
| (b) | Macrogol 4000 BP | 350 |
| | | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with release-controlling membrane (d) and filled into a two-piece, hard gelatin capsule.

|  |  | mg/capsule |
|---|---|---|
| (a) | Active Ingredient | 250 |
| (b) | Microcrystalline Cellulose | 125 |
| (c) | Lactose BP | 125 |
| (d) | Ethyl Cellulose | 13 |
|  |  | 513 |

EXAMPLE 46 INJECTABLE FORMULATION

| Formulation A | |
|---|---|
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B | |
|---|---|
| Active ingredient | 0.125 g |
| Sterile, pyrogen-free, pH 7 phosphate buffer, | q.s. to 25 ml |

EXAMPLE 47 INTRAMUSCULAR INJECTION

| Active Ingredient | | 0.20 g |
|---|---|---|
| Benzyl Alcohol | | 0.10 g |
| Glycofurol 75 | | 1.45 g |
| Water for Injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 48 SYRUP

| Active ingredient | | 0.25 g |
|---|---|---|
| Sorbitol Solution | | 1.50 g |
| Glycerol | | 2.00 g |
| Sodium Benzoate | | 0.005 g |
| Flavour, Peach 17.42.3169 | | 0.0125 ml |
| Purified Water | q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 49 POWDER CAPSULES FOR INHALATION

| Active Ingredient (0.5–.70 μm powder) | 4 mg |
|---|---|
| Lactose (30–90 μm powder) | 46.0 mg |

The powders were mixed until homogeneous and filled into suitably sized hard gelatin capsules, 50 mg of mixture per capsule.

EXAMPLE 50 INHALATION AEROSOL

| Active Ingredient (0.5–7.0 μm powder) | | 200 mg |
|---|---|---|
| Sorbitan Trioleate | | 100 mg |
| Saccharin Sodium (0.5–7.0 μm powder) | | 5 mg |
| Methanol | | 2 mg |
| Trichlorofluoromethane | | 4.2 g |
| Dichlorodifluoromethane | to | 10.0 ml |

The Sorbitan Trioleate and Menthol were dissolved in the Trichlorofluoromethane. The Saccharin Sodium and active ingredient were dispersed in the mixture which was then transferred to a suitable aerosol canister and the Dichlorofluoromethane injected through the valve system. This composition provides 2 mg of active ingredient in each 100 μl dose.

Antiviral Activity

Influenza A and B strains were assayed in monolayers of primary chick embryo(ce) cells in multiwell trays. Activity of compounds was determined in the yield reduction or in the plaque reduction assay, in which a cell monolayer was infected with a suspension of influenza virus and then overlaid with liquid medium (yield reduction) or with nutrient agarose in the form of a gel to ensure that there is no spread of virus throughout the culture (plaque reduction). A range of concentration of compound of known molarity was incorporated into the medium/nutrient agarose overlay. Yield of virus or plaque numbers of each concentration are expressed as a percentage of the control and a does response curve is drawn. From this curve the 50% inhibitory concentration ($IC_{50}$) is estimated. Respiratory Syncytial Virus (RSV) is assayed in BS-C-1 cells (African Green Monkey kidney cells) by a similar plaque/foci reduction assay. The results are presented in Tables I and II below.

In vivo inhibitory activity was assessed for Influenza A and B strains in a mouse intranasal/lung model. Mice were infected with virus by aerosol in an enclosed box and then treated with test compounds at various times after infection by various routes, including oral, intraperitonally and by aerosol. The mice were sacrificed after 24 hours and 10% lung suspensions prepared and titrated for presence of virus. Results were recorded as a reduction in virus growth compared with untreated controls.

References

Appleyard, G and Maber, H. B, Plaque Formation by Influenza Vi-ruses in the Presence of Trypsin. J. Gen. Virol. 25, 351–357. (1974). Collins, P. and Bauer, D. J, Relative Potencies of Anti-Herpes Compounds. Ann. N.Y. Acad. Sci. 284, 49–59, (1977). Hayden, F. G, Cotek, M. and Douglas, R. G., Plaque Inhibition Assay for Drug Susceptibility Testing of Influenza Viruses. Antimicro Agents and Chemo. 17. 865–870. (1980).

Tisdale, M. and Bauer, D. J. A comparison of test methods in influenza chemotherapy. J. Antimicrobio. Chemother. 1 suppl. 55–62 (1975).

TABLE I

| Ex.No. | Compound | | | | Anti-influenza Activity | |
|---|---|---|---|---|---|---|
| | R1 | R2 | X | Y | CE cells $IC_{50}$, μM | Mouse log10 reduction in virus titre. (Average of 5 Mice) |
| 6 | OH | OH | $NH_2$ | $NH_2$ | 0.6 | +(2.1) |
| 7 | OH | OH | OH | $NH_2$ | 0.8–2 | +(2.4) |
| 8 | OH | OH | $NH_2$ | H | 4 | +(2.3) |
| 9 | OH | OH | H | $NH_2$ | — | +(1.6) |
| 12 | OH | OH | OMe | $NH_2$ | 0.4 | +(1.9) |

| Ex.No. | Compound | | | | Anti-respiratory syncytial virus |
|---|---|---|---|---|---|
| | | | | | BS-C-1 cells $IC_{50}$ μM |
| 7 | OH | OH | OH | $NH_2$ | 26.2 |
| 12 | OH | OH | OMe | $NH_2$ | 6.3 |

We claim:

1. A method of treating a *Trichomonas vaginalis* infection in a mammal in need thereof which comprises administering to said mammal a therapeutically effective amount of the compound selected from the group consisting of:

2,6-Diamino-9-(2-deoxy-2-fluoro-β-D-ribofuranosyl)-9H-purine or a pharmaceutically acceptable salt thereof, 2-Amino-9-(2-deoxy-2-fluoro-β-D-ribofuranosyl)-9H-purine or a pharmaceutically acceptable salt thereof, and 2-Amino-9-(2-deoxy-2-fluoro-β-D-ribofuranosyl)-6-methoxy-9H-purine or a pharmaceutically acceptable salt thereof.

2. The method of claim 1 in which the amount administered per day is 10 to 150 mg/kg based on mammal bodyweight.

3. The method of claim 2 in which the amount administered per day is 25 to 75 mg/kg based on mammal bodyweight per day.

4. A method of treating a *Giardia lamblia* infection in a mammal in need thereof which comprises administering to said mammal a therapeutically effective amount of the compound selected from the group consisting of:

2,6-Diamino-9-(2-deoxy-2-fluoro-β-D-ribofuranosyl)-9H-purine or a pharmaceutically acceptable salt thereof, 2-Amino-9-(2-deoxy-2-fluoro-β-D-ribofuranosyl)-9H-purine or a pharmaceutically acceptable salt thereof, and 2-Amino-9-(2-deoxy-2-fluoro-β-D-ribofuranosyl)-6-methoxy-9H-purine or a pharmaceutically acceptable salt thereof.

5. The method of claim 4 in which the amount of the compound or salt administered per day is 10 to 150 mg/kg based on mammal bodyweight.

6. The method of claim 5 in which the amount is 25 to 75 mg/kg.

* * * * *